United States Patent
Yamazaki (12)

(10) Patent No.: US 6,336,899 B1
(45) Date of Patent: Jan. 8, 2002

(54) ULTRASONIC DIAGNOSIS APPARATUS

(75) Inventor: Nobuo Yamazaki, Otawara (JP)

(73) Assignee: Kabushiki Kaisha Toshiba, Kawasaki (JP)

(*) Notice: Subject to any disclaimer, the term of this patent is extended or adjusted under 35 U.S.C. 154(b) by 0 days.

(21) Appl. No.: 09/390,300

(22) Filed: Sep. 3, 1999

(30) Foreign Application Priority Data

Oct. 14, 1998 (JP) .......................................... 10-292619
May 21, 1999 (JP) .......................................... 11-142102

(51) Int. Cl.[7] .............................. A61B 8/00; A61B 8/14
(52) U.S. Cl. ...................... 600/443; 600/461; 128/916
(58) Field of Search .............................. 600/437, 461, 600/439, 463, 425, 464, 562, 466, 462, 471, 443, 447; 128/916

(56) References Cited

U.S. PATENT DOCUMENTS

| | | | |
|---|---|---|---|
| 5,131,397 A | * 7/1992 | Crowley | 600/462 |
| 5,660,185 A | * 8/1997 | Schmulewitz et al. | 600/562 |
| 5,851,183 A | * 12/1998 | Bucholz | 600/425 |
| 6,019,725 A | * 2/2000 | Vesely et al. | 600/447 |
| 6,048,312 A | * 4/2000 | Ishrak et al. | 600/443 |
| 6,066,096 A | * 5/2000 | Smith et al. | 600/439 |
| 6,126,600 A | * 10/2000 | Oxaal et al. | 600/439 |

FOREIGN PATENT DOCUMENTS

| | | |
|---|---|---|
| JP | 7-8497 | 1/1995 |
| JP | 11-164833 | 6/1999 |

* cited by examiner

*Primary Examiner*—Brian L. Casler
*Assistant Examiner*—Ali M. Imam
(74) *Attorney, Agent, or Firm*—Oblon, Spivak, McClelland, Maier & Neustadt, P.C.

(57) ABSTRACT

An ultrasonic diagnosis apparatus which includes a plurality of ultrasonic transducers arranged two-dimensionally. In the ultrasonic diagnosis apparatus, the ultrasonic beams are transmitted by the ultrasonic transducers for three-dimensionally scanning a target of the object, and then, ultrasonic echo signals are obtained from the ultrasonic transducers. On the basis of the ultrasonic echo signals, three-dimensional data with respect to at least one of structure information and blood flow information in the object are generated in real time. Then, on the basis of the three-dimensional data, image information including at least one of a two-dimensional tomographic image and a three-dimensional projection image of an arbitrary cross section within the object is generated in real time. On the basis of the image information, navigation information for navigating a puncture needle toward the target of the object is displayed.

30 Claims, 25 Drawing Sheets

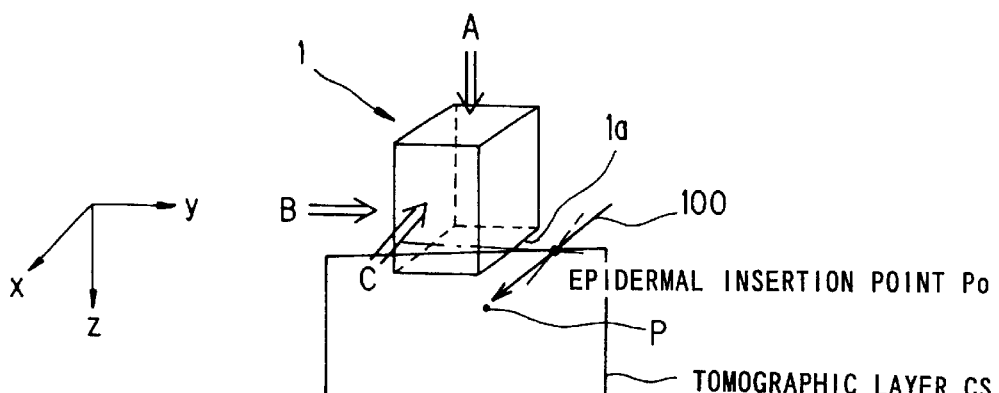
FIG. 6A
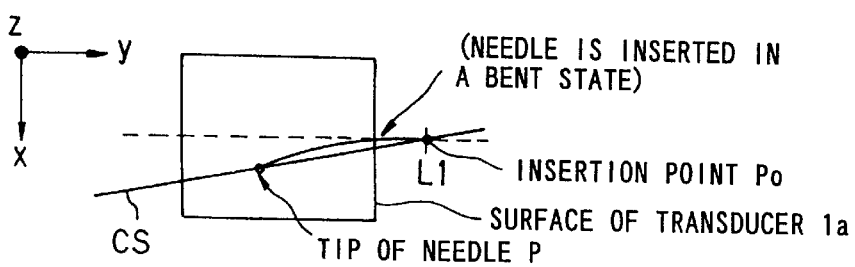
FIG. 6B  PLANE VIEW SEEN A IN (a)
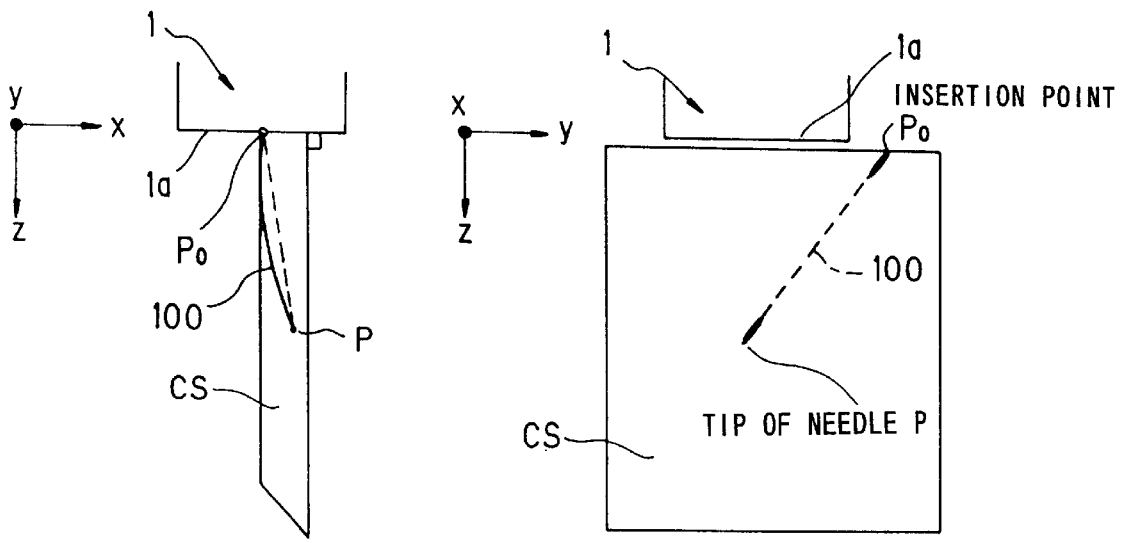
PLANE VIEW SEEN B IN (a)
FIG. 6C
PLANE VIEW SEEN C IN (a)
FIG. 6D FIG. 12B  PLANE VIEW SEEN FROM A IN (a)

PLANE VIEW SEEN FROM B IN (a)

PLANE VIEW SEEN FROM C IN (a)

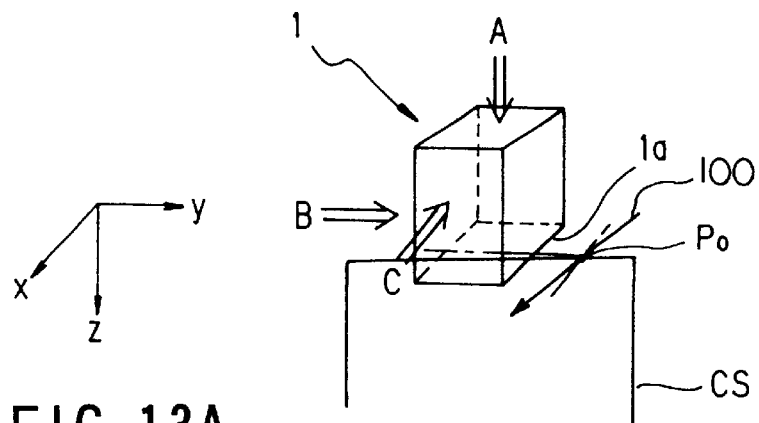
FIG. 13A
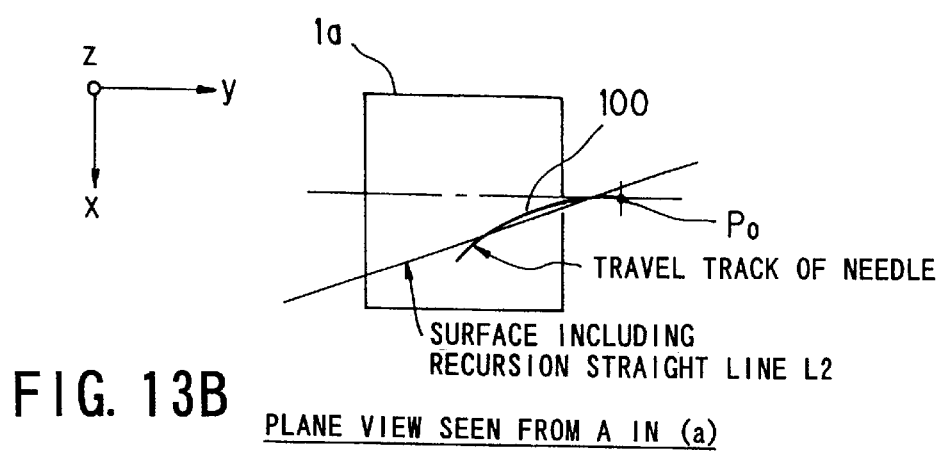
FIG. 13B PLANE VIEW SEEN FROM A IN (a)
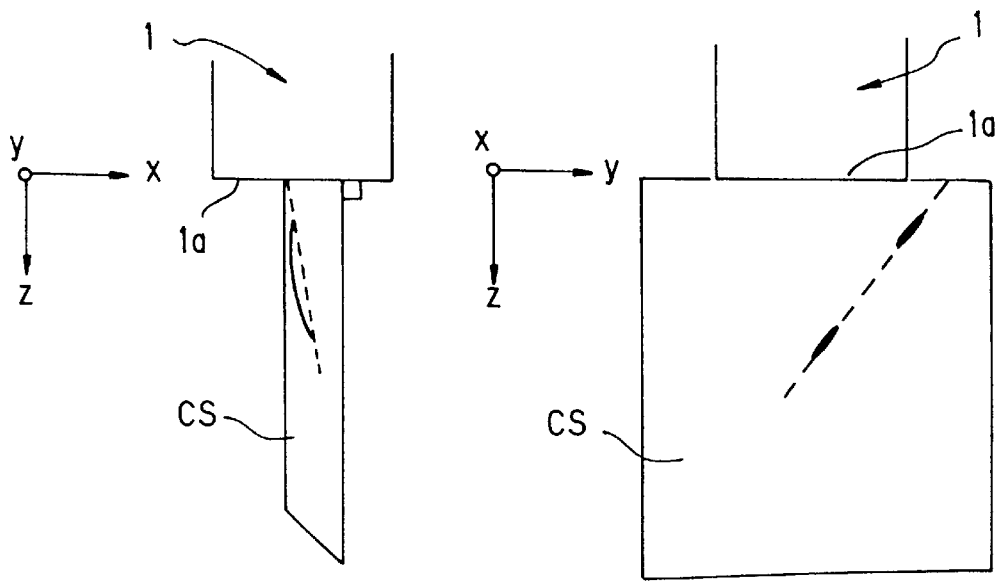
PLANE VIEW SEEN FROM B IN (a)
PLANE VIEW SEEN FROM C IN (a)
FIG. 13C
FIG. 13D FIG. 14B  PLANE VIEW SEEN FROM A IN (a)

PLANE VIEW SEEN FROM B IN (a)

PLANE VIEW SEEN FROM C IN (a)

ULTRASONIC DIAGNOSIS APPARATUS

BACKGROUND OF THE INVENTION

The present invention relates to an ultrasonic diagnosis apparatus, which is capable of scanning ultrasonic beams in three-dimensional configuration in real time and displaying a three-dimensional image thereof, and more particularly, to an apparatus for navigating a paracentetic needle toward a target such as lesion or the like in a object while watching an ultrasonic image.

In the biopsy of the liver in the clinical application, namely the biopsy for diagnosing the property of the parenchyma of hepar, the biopsy for diagnosing the property of the tumor or the like, or a treatment method of liver cancer in the treatment application, namely a method for forcing hepatoma cells to necrose by pouring ethanol into the hepatoma, a diagnosis and a treatment are generally performed by inserting a paracentetic needle into the inside of the body of the patent (hereinafter referred to as paracentisis).

In this paracentsis, conventionally various kinds of paracentisis methods have been invented, and have been applied to the diagnosis and the treatment. Except for the case in which the paracentetic needle may be penetrated into the body in a blind manner, it often happens that the paracentisis is performed together with a monitoring method in which a paracentetic target such as lesion or the like is confirmed while an image such as X-ray photofluorograph image or the like is observed in real time. Particularly, in recent years, in order to further heighten the safety and reliability of the treatment, diagnostic treatment skill (hereinafter referred to as the ultrasonic paracentisis) has become a major method in which the paracentetic needle is guided by using ultrasonic images in the place of X ray fluorograms.

This ultrasonic paracentisis is a paracentisis using images in which both the paracentetic target and the paracentetic needle are drawn out on the same tomographic layer of a real time ultrasonic image so that the treatment is performed while watching the travel of the paracentetic needle. For example, in the case of the abdomen, major blood vessels inside and outside of the liver and peripheral organs can be easily drawn out together with dilated bile ducts and gall bladders as ultrasonic tomographic images. As a consequence, there is provided an advantage in that a selective paracentisis can be performed in which the paracentetic target can be arbitrarily selected and the paracentetic needle can be penetrated thereinto with the result that the scope of the clinical application and the treatment application is widened. For example, in the application of the ultrasonic paracentisis in liver diseases, a reliable paracentisis of the tumor can be performed with respect to a localized lesion. Besides, a route for paracentisis can be selected while deviating around gall bladders and the lungs with the result that there is provided an advantage in that the paracentisis will contribute toward the reduction in complications such as choleperitoneum, hemopneumothrax or the like.

As an ultrasonic device which is used in such ultrasonic paracentisis, a mechanical scanning type or an electronic scanning type real-time devices are adopted. In these real-time devices, a sector or a convex probe or the like is used which allows the attachment of a linear probe exclusively used for paracentisis as an ultrasonic probe and a paracentetic adapter for guiding the paracentetic needle in a definite direction. Particularly, in recent years, the electronic scanning type device becomes prevalent, and an electronic linear probe or an electronic sector probe is used in many cases along with the usage of the real-time devices.

With all the advantages of safety and a high reliability as compared with X ray flurograph or the like, the ultrasonic beams device which is used in the conventional ultrasonic paracentisis has a problem in that since the paracentetic needle is elastic, the direction of the needle tip is sometimes deviated from the guide direction. In such a case, since the Up of the paracentetic needle disappears from the inside of the two-dimensional tomographic image which is displayed in real time, the position of the tip of the needle must be searched while allowing the ultrasonic probe to be operated. As a consequence, there arises a problem that an operation of trading the position of the tip of the needle and correcting the insertion direction of the needle which is directed toward the paracentetic target such as the lesion or the like while observing the two-dimensional tomographic image becomes difficult in may cases with the result that a considerable amount of training is required for such an operation.

SUMMARY OF THE INVENTION

Accordingly, it is an object of the present invention to provide an ultrasonic diagnosis apparatus for easily and reliably guide the paracentetic needle at the time of using the ultrasonic paracentisis.

The inventors of the present invention studied in detail more safe and accurate paracentetic needle guiding means with respect to the paracentisis method which is combined with the ultrasonic diagnosis apparatus, and they noted a method for navigating a paracentetic needle toward a paracentetic target while confirming the position of the paracentetic needle on a three-dimensional image by combining the paracentisis method with an ultrasonic beams device which is capable of scanning ultrasonic beams in a three-dimensional manner in real time and displaying the three-dimensional image (3D image).

The method for navigating the paracentetic needle using this 3D image is constituted centering on the following four points: 1) a method for displaying a tomographic image (a method for displaying a tomographic image which is appropriate for recognizing a position relation between a direction in which the tip of the needle is directed and a lesion which is selected as a paracentetic target), 2) a method for detecting the position of the needle and a track of the movement of the needle, 3) a three-dimensional display method (a display method in which the direction in which the tip of the needle is directed is seen from just above), and 4) a method for recognizing a 3D image, the position of the object and the direction relation thereof. Concrete examples of the aforementioned methods will be explained hereinbelow.

1) Method for Displaying Tomographic Image

Even in the case where the tip of the needle is deviated from a guide direction of a paracentetic adapter and in the case where the needle is penetrated without a guide for paracentisis, this method for displaying the tomographic image enables 1a) displaying a location of the tip of the needle constantly within the tomographic image and displaying a location (region) toward which the tip of the needle is directed, 1b) visibly recognizing whether or not the tip of the needle or the whole needle is located in front of or at the rear surface of the tomographic layer or how much the tip of the needle or the whole needle is deviated from the tomographic layer without changing a tomographic by layer which is set at first, namely, by an image in which a lesion constituting a paracentetic target is caught.

For example, as the tomographic layer 1a), there is available 1a-1) a surface (into which a straight line enters)

which contacts a straight line connecting a tip point of the needle and a insertion point of the needle into the living body, and, at the same time, a surface which is vertical with respect to a surface of a transducer of a ultrasonic probe, 1a-2) a surface which passes through a tip of a needle, an insertion point of the needle into the living body, and a reference point (for example, a central point of a surface of a transducer), 1a-3) a surface (into which a straight line enters) which contacts a line obtained by a straight line recursion by sampling the tip of the needle, and at the same time, a surface which is vertical with respect to the surface of the transducer, and 1a-4) a surface which passes through a reference point (for example, a central point of the transducer) by sampling the tip of the needle and allowing the line obtained in the straight line recursion to serve as one side.

Besides, the aforementioned method 1b) enables 1b-1) displaying each part of the needle by changing the color thereof on the image in the case where the position of the needle exists in front of the tomographic layer on which the position is displayed and in the case where the position of the needle is present at the rear surface of the tomographic layer (for example, the color of the needle is set to red in the case where the needle is present in front of the tomographic layer while the color is set to blue in the case where the needle is present at the rear surface of the tomographic layer so that the colors are overlapped on a white and black image on which the needle is displayed thereby displaying only the white and black image only when the needle coincides with the tomographic layer), and 1b-2) displaying how much the needle is separated from the tomographic layer by changing the hue.

2) Method for detecting and Tracing the Position of the Needle and the Track of the Movement of the Needle In this detection method, 2a) a signal generation source is attached on the tip of the needle so that a signal which is generated from this generation source is received with three or more devices (such as a ultrasonic beams transducer or the like), and the three-dimensional position of the tip of the needle is inferred on the basis of the time difference of the received signal, 2b) a plurality of signal generation sources are attached on different positions of the needle in addition to the tip of the needle so that the three-dimensional position of the whole needle is inferred on the basis of the signal generated from this plurality of generation sources, 2c) a condition under which a strength of an echo signal from the needle becomes the highest is searched by exciting ultrasonic beams in the vicinity of a location where the needle is placed so that the position of the needle is inferred on the basis of the condition, 2d) a condition under which a strength (power) of a Doppler signal becomes the highest is searched by allowing the needle to vibrate minutely and exciting ultrasonic beams in the vicinity a location where the needle is placed so that the position of the needle is inferred on the basis of the condition, and 2e) a track of the movement of the needle tip is traced by means of a signal processing or an image processing (for example, a cross correlation method).

3) Three-dimensional Display Method

This three-dimensional display method provides a display of a three-dimensional projection image as seen from just above in which the direction in which the tip of the needle is directed; for example, 3a) a 3D projection image of the blood vessels is shown plus a 3D projection image of the needle plus a B mode tomographic image of a lesion which is selected as a target, 3b) the 3D projection image of the blood vessels is shown plus a 3D projection image of the needle plus a B mode 3D image (boundary surface) of a lesion which is selected as a target, and 3c) the 3D projection image of the blood vessels is shown plus the 3D projection image of he needle plus the B mode 3D image of a lesion which is selected as a target plus the B mode tomographic image of the tip part of the needle.

4) Method for Recognizing 3D Image, the Position of the Living body and the Direction Relation Thereof In this recognition method, 4a) parts of the paracentetic needle contain a mark indicative of a direction, for example, a cross-shaped member is attached on a tip part on the side of the insertion operation of the paracentetic needle to display a marker which enables correlating the position relation with the marker, 4b) a marker is displayed which enables recognizing where the tomographic image in the aforementioned 1) is sectioned on the three-dimensional image in the aforementioned 3).

The ultrasonic diagnosis apparatus according to the present invention has been completed on the basis of the aforementioned idea, and is characterized by comprising:

data obtaining means having a plurality of ultrasonic transducers arranged in a two-dimensional configuration, the means obtaining an echo signal of an ultrasonic beams while allowing beams of the ultrasonic beams transmitted from each of the ultrasonic beams transducers to be scanned in a object;

means for analyzing in real time three-dimensional data with respect to at least one of geometry information and blood flow information in the aforementioned object on the basis of the echo signal of the ultrasonic beams obtained by the data obtaining means;

means for generating in real time an image including at least one of a two-dimensional tomographic image and a three-dimensional projection image of an arbitrary cross section within the aforementioned object on the basis of the three-dimensional data analyzed by the data analyzing means; and means for displaying navigation information for navigating a medical insert toward a target within the aforementioned object on the basis of the image information generated by the ultrasonic image generating means. The aforementioned medical insert is, for example, a paracentetic needle which is inserted into the body from the epidermal part of the aforementioned object.

Preferably, according to the present invention, the aforementioned navigation means is characterized by comprising tracing means for detecting a movement position at each moment of the paracentetic needle inserted into the aforementioned object thereby tracing a track of the movement of the paracentetic needle, and image display control means for controlling in real time an image display condition so that the travel state of the paracentetic needle toward a target within the aforementioned object can be constantly recognized in the aforementioned image.

BRIEF DESCRIPTION OF THE DRAWINGS

The accompanying drawing which are incorporated in and constitute a part of this specification, illustrate embodiments of the present invention and, together with the description, serve to explain the principles of the present invention; in which:

FIG. 4A is a view for explaining the concept thereof, and FIG. 4B is an outline timing chart for explaining a difference in signal arrival times;

FIGS. 6A to 6D are views for explaining a method for setting a cross section of a two-dimensional tomographic image;

FIG. 8A is an outline view showing a plurality of transmission positions, and FIG. 8B is an outline timing chart for explaining a difference in the signal arrival times from a plurality of transmission positions;

FIG. 9A is an outline view showing a plurality of cross sections within a three-dimensional volume scan, and FIG. 9B is an outline timing chart showing the strength of the echo signal for each of the plurality of tomographic images;

FIG. 10A is an outline view showing a plurality of cross sections within the three-dimensional volume scan, and FIG. 10B is an outline timing chart showing the power of the Doppler signal for each of the plurality of cross sections;

FIGS. 12A to 12D are views for explaining a method for setting a cross section of a surface including a center of gravity of a surface of the transducer;

FIGS. 13A to 13D are views for explaining a method for setting a cross section of a surface including a recursion straight line of a travel track of the paracentetic needle;

FIGS. 14A to 14D are views for explaining a method for setting a cross section of a surface including the center of the gravity on the surface of the transducer and the recursion straight line of the travel track of the paracentetic needle;

DESCRIPTION OF THE PREFERRED EMBODIMENTS

Figure 1:
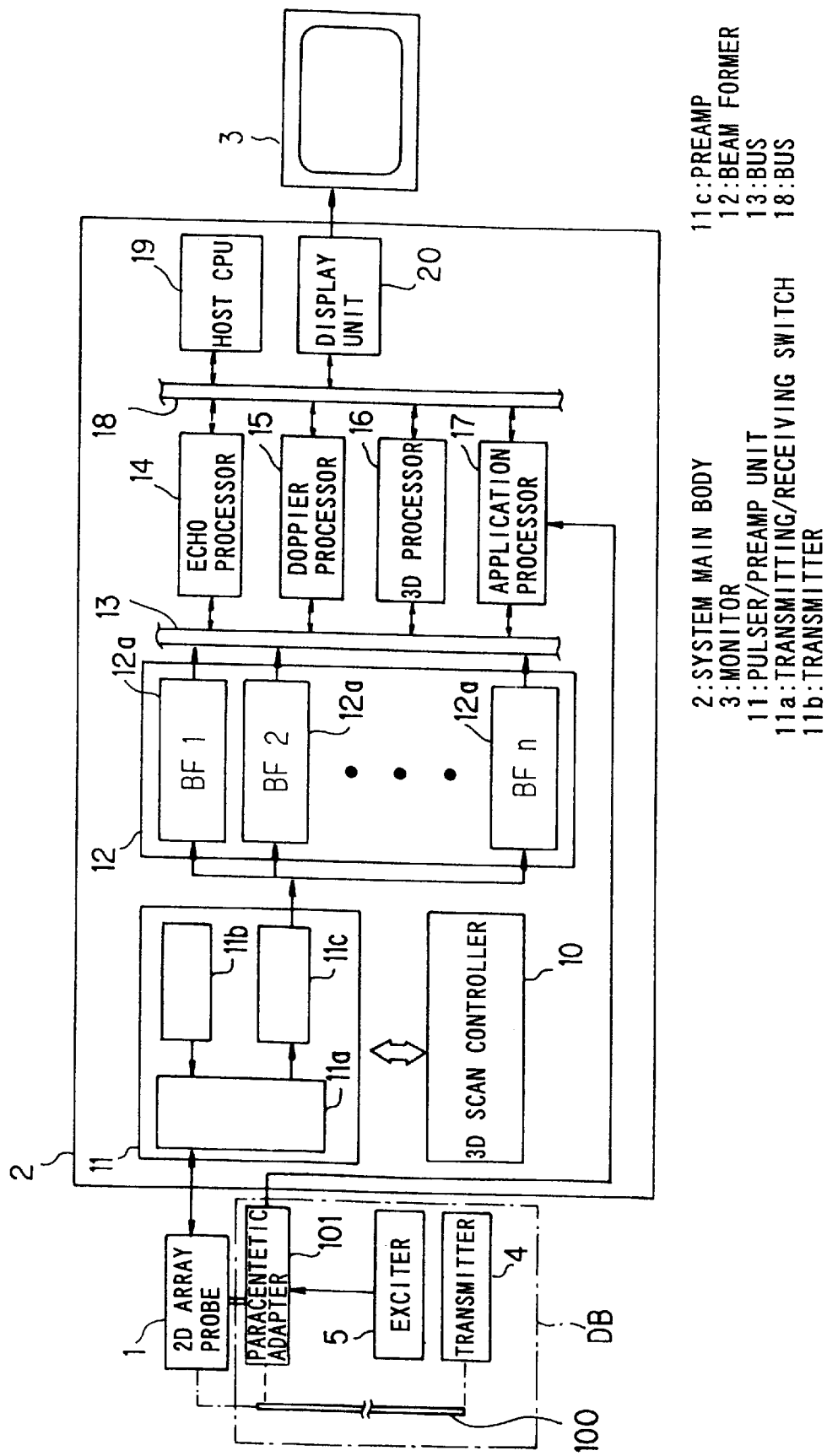
FIG. 1 is a block view showing an outline structure of an ultrasonic diagnosis apparatus according to the invention, the view explaining an embodiment of the ultrasonic diagnosis apparatus according to the present invention.

Embodiments of an ultrasonic diagnosis apparatus according to the present invention will be explained by referring to the drawings.

Figure 2:
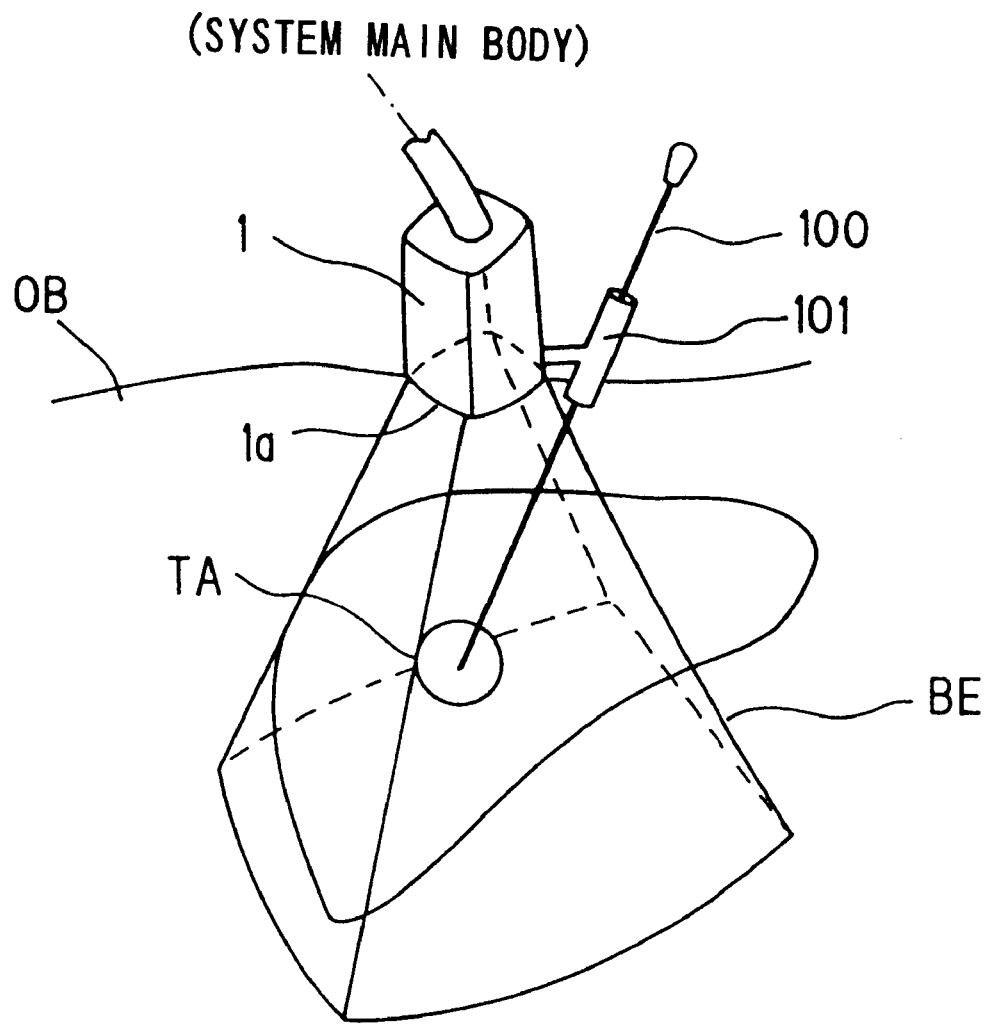
FIG. 2 is a perspective view for explaining a concept of a three-dimensional volume scan and the paracentisis.

The ultrasonic diagnosis apparatus shown in FIGS. 1 and 2 is intended to execute the paracentisis method by using a paracentetic needle device DB having a paracentetic needle 100 and a paracentetic adapter 101 for guiding the paracentetic needle 100. The needle 100 can be inserted from an epidermal part of a object OB into a lesion such as tumor inside the body or the like selected as a target TA in a progressive and a regressive direction The ultrasonic diagnosis apparatus is provided with a two-dimensional array probe (ultrasonic probe) 1 on which the paracentetic adapter 101 is attached in a detachable manner and fixed, a system main body 2 to which this probe 1 is connected, and a monitor thereof 3.

Here, at a tip part of the paracentetic needle 100 which corresponds to a puncture needle of the present invention, a transmitter (signal generator) 4 constituting part of the tracing means of the present invention is provided so that a signal from this transmitter 4 can be received with the two-dimensional array probe 1. Furthermore, as another example of the tracing means according to the present invention, an exciter 5 which gives a minute vibration to the paracentetic needle 100 in an inserted state is attached on the paracentetic adapter 101 so that the two-dimensional array probe 1 can receive an echo signal which is affected by a Doppler effect of the paracentetic needle 100 which is vibrated with this exciter 5.

The two-dimensional array probe 1 is constituted, for example, with an arrangement of a plurality of ultrasonic transducers in two-dimensional configuration. Each of the ultrasonic transducers is driven with the system main body 2 under the predetermined three-dimensional scanning condition with the result that, as shown in FIG. 2, ultrasonic beams BE are scanned in three-dimensional configuration with respect to the target TA inside the object OB from the surface of the transducer (transducer arrangement surface) 1a, namely, the ultrasonic beams are scanned in three-dimensional configuration, thereby converting the echo signal of the ultrasonic beams into an echo signal of having a feeble voltage amount, detecting the echo signal, and sending the echo signal into the system main body 2.

The system main body 2 includes a three-dimensional scan controller 10 for controlling the three volume scan by means of the two-dimensional array probe 1 and a pulser/ preamplifier unit (a transmitting/receiving change-over switch 11a, a transmitter 11b, and a preamplifier 11c) 11 which constitutes a ultrasonic transmitting and receiving system which electronically drives the two-dimensional array probe 1 under the control of this controller 10. The pulser/ preamplifier unit 11 generates a drive pulse with the transmitter 11b on the basis of the drive condition for three-dimensional scanning which is preset with the three-dimensional scan controller 10 with the result that this pulse is sent to the two-dimensional array probe 1 via the transmitting/receiving change-over switch 11a, and, at the same time, the echo signal which is received with this probe 1 is received with the preamplifier 11c via the transmitting/ receiving change-over switch 11a.

Then, the system main body 2 is provided with a unit 12 comprising a plurality (n) of beam formers (BF1 . . . . BFn) 12a . . . 12n for phasing addition on the side of the output of the aforementioned preamplifier 11c, and a group of processors connected via a bus 13 on the side of the output of this unit 12, namely an echo processor 14 for analyzing 3D data with respect to a B mode image which enables grasping geometries such as organs inside of the object and the running of the blood vessels or the like from information on an acoustic impedance in the echo signal, a Doppler processor 15 for obtaining 3D data with respect to information on the blood flow rate or the like of the object from the frequency analysis by extracting a Doppler signal from the echo signal, a 3D processor 16 for constructing a 3D image (which includes at least one of the two-dimensional tomographic image and the three-dimensional projection image of an arbitrary cross section) on the basis of these items of 3D data, an application processor (an essential part of the navigating means of the present invention) 17 for controlling an image processing for the navigation support of the paracentetic needle 100, a host CPU 19 for the whole control connected to the group of processors via the bus 18 for controlling the whole system, and a display unit 20 which is concerned with the image display. A monitor 3 is connected to an output side of the display unit 20.

Here, an overall operation will be explained centering on a processing by the application processor 17 on the basis of FIGS. 3 to 7.

In the beginning, at the time of starting the device, a drive pulse from the transmitter 11b is sent to the two-dimensional array probe 1 under the control of the three-dimensional scan controller 10 inside of the system main body 2 via the transmission/receiving change-over switch 11 a so that the ultrasonic beams BE from each of the ultrasonic beams transducers are scanned in the three-dimensional configuration in a region which covers the target TA inside of the object OB.

Next, the echo signal of the ultrasonic beams is converted into a feeble voltage echo signal with the two-dimensional array probe 1 to be detected so that the echo signal is amplified with the preamplifier via the transmitting/ receiving change-over switch 11a so that the phasing addition is carried out with the beam former unit 12, and at least one of the 3D data is analyzed; under the control of the host CPU 19, either the B mode image is analyzed with the echo processor 14 or information on the blood flow is analyzed with the Doppler processor 15. Then, the 3D image is prepared on the basis of the 3D data with the 3D processor 16, and is displayed on the monitor 3 via the display unit 20.

The ultrasonic paracentisis by the operator is initiated while this monitor 3 is being observed. At the time of starting the paracentsis, the paracentetic needle 100 is inserted toward the target TA inside of the body from the epidermal part of the object OB via the paracentetic adapter 101. While this paracentetic needle 100 is inserted into the object OB, the signal which is transmitted at a predetermined timing from the transmitter 4 attached on the tip position of the paracentetic needle 100 is received with the two-dimensional array probe 1, and, at the same time, an algorithm for the navigation support is executed in real time with the application processor 17. This algorithm includes a processing for tracing the paracentetic needle 100 constituting an essential part of the tracing means of the present invention (refer to FIGS. 3 and 4) and a display control processing (refer to FIGS. 5 through 7) of the 3D image constituting an essential part of the image display control means of the present invention.

Figure 3:
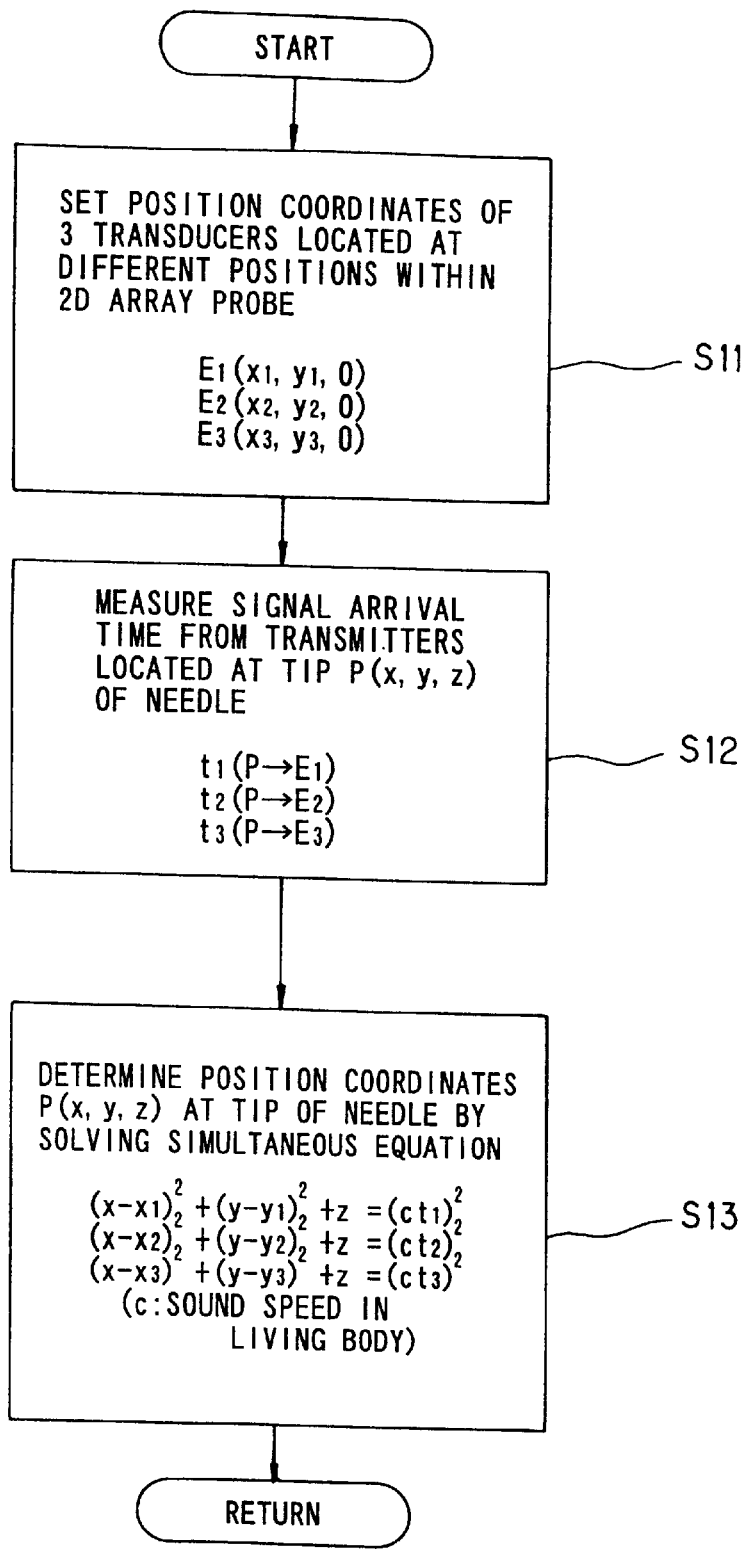
FIG. 3 is an outline flowchart showing a tracing processing by means of an application processor.
Figure 4A:
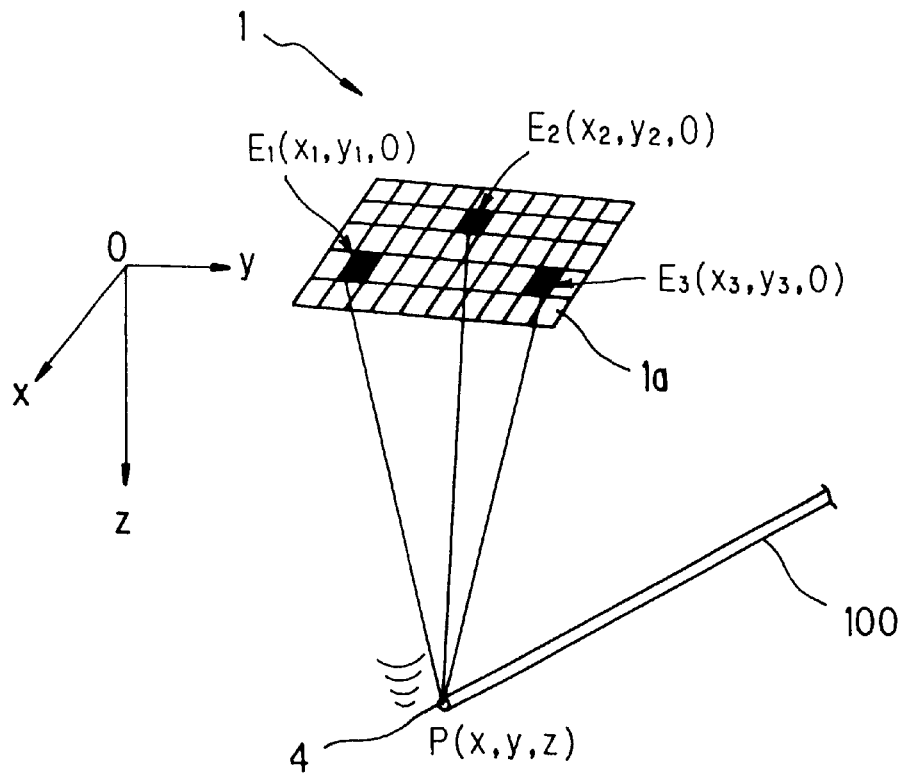
FIGS. 4A and 4B are views for explaining a processing for tracing a tip of the paracentetic needle using a transmitter.
Figure 4B:
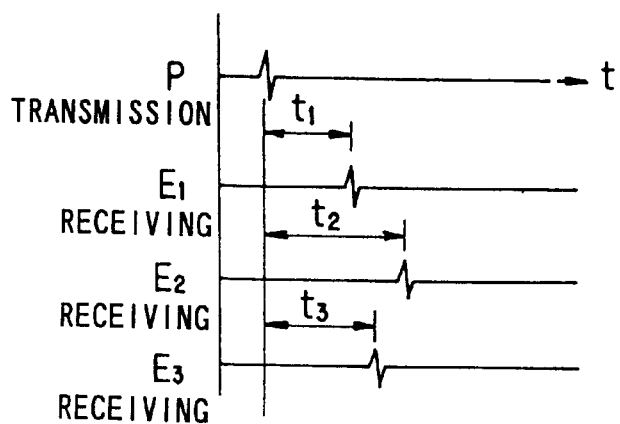

In the beginning, with the application processor 17, processings at the steps S11 to S13 shown in FIG. 3 are executed. In other words, at the step S11, the position coordinates E1 (x1, y1, 0), E2(x2, y2, 0), and E3(x3, y3, 0) in three transducers located at different positions within the two-dimensional array probe 1 are initialized. (In this case, the surface of the transducer 1a corresponds to xy surface). The position relation between the three transducers E1, E2 and E3 is shown in a concept view of FIG. 4A.

Next, at the step S12, the signal arrival times t1, t2 and t3 from the transmitter 4 located at the tip position P (x, y, z) of the paracentetic needle 101 up to the three transducers E1, E2 and E3 are measured. These signal arrival times t1, t2 and t3 are different by reflecting the difference in positions of each of the transducers E1, E2 and E3. The state is shown in a timing chart of FIG. 4B.

Next, at the step S12, the signal arrival times t1, t2 and t3 from the transmitter 4 located at the tip position P (x, y, z) of the paracentetic needle 100 up to the three transducers E1, E2 and E3 are measured. These signal arrival times t1, t2 and t3 are different by reflecting the difference in positions of each of the transducers E1, E2 and E3. The state is shown in a timing chart of FIG. 4B.

Next, unknown numbers x, y and z, namely, the tip positions P(x, y, z) are determined by solving, at the step SI 3, a simultaneous equation established between a $$(x-x1)^2+(y-y1)^2+z2=(ct1)^2$$

$$(x-x2)^2+(y-y2)^2+z2=(ct2)^2$$

$$(x-x3)^2+(y-y3)^2+z2=(ct3)^2$$

sound speed c within a living body, each of the signal arrival times t1, t2 and t3 having a time difference, fixed numbers x1 to x3, y1 to y3, z1 to z3 of the position coordinates of the probe transducer, the unknown numbers x, y and z of the position coordinates of the tip position P of the paracentetic needle 100. The simultaneous equation is given below.

In this manner, the processings at the steps S11 through S13 are executed in a repeated manner for determining P(x, y, z) with the result that the movement position of the paracentetic needle 100 can be constantly detected and traced.

Figure 5:
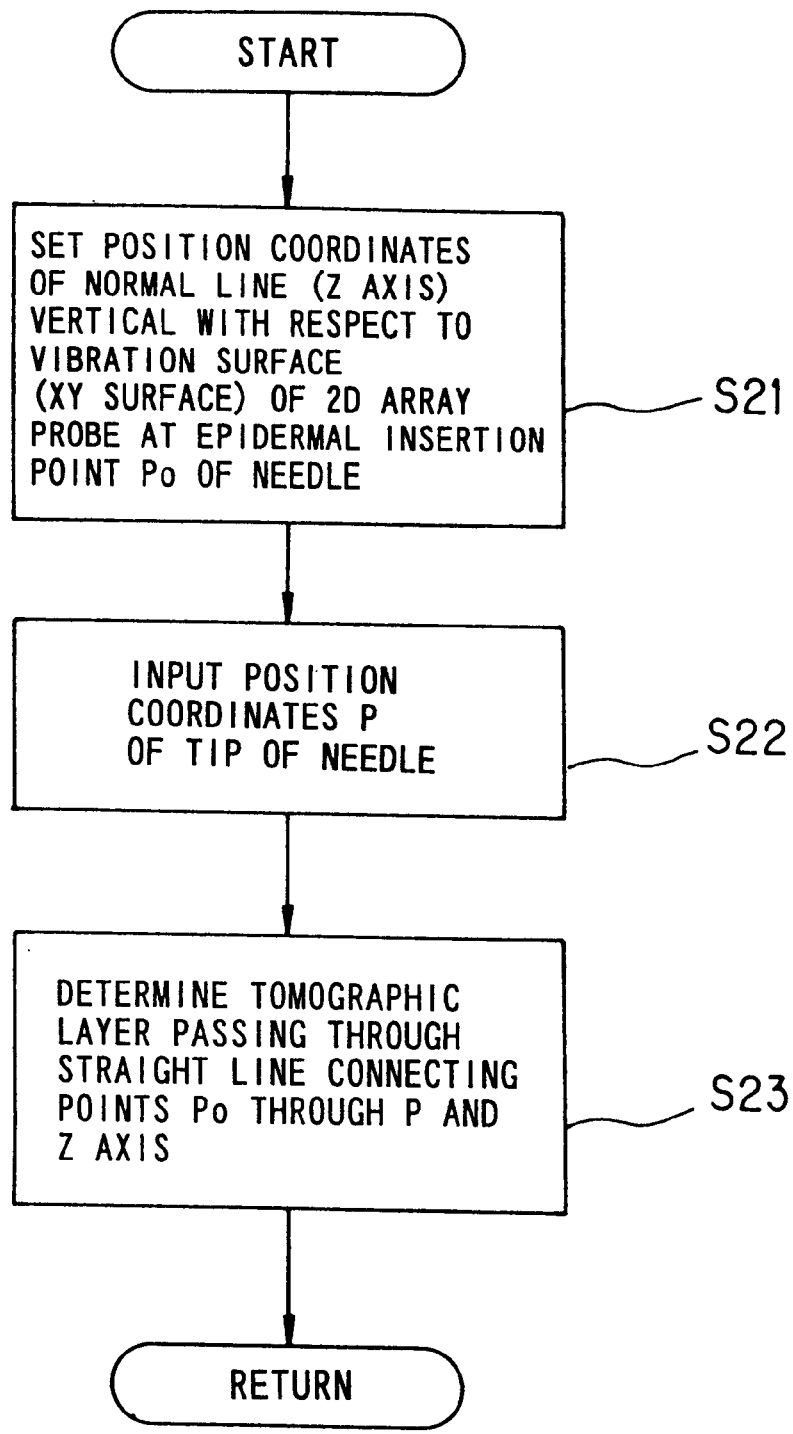
FIG. 5 is an outline flowchart showing a 3D image display control processing of an application processor.

Along with this, with the application processor 17, the 3D image display control processing at the steps S21 through S23 shown in FIG. 5 are executed. In other words, at the step S21, the epidermal insertion point P0 of the paracentetic needle 100 and a normal line (z axis) which is vertical with respect to the surface (xy surface) 1a of the transducer of the two-dimensional array probe 1 are initiated. At the step S22, the tip position P of the paracentetic needle which point is determined at the aforementioned step S11 to 13 is input, and at the step S23, a tomographic layer (cross section) CS is determined which passes through a straight line L1 connecting the epidermal insertion point P0 of the paracentetic needle 100 with the tip position P of the needle and a normal line which is vertical with respect to the surface 1a of the transducer. The position relation thereof will be shown in FIGS. 6A through 6D.

On the tomographic layer SC which is determined in this manner, not only the tip of the needle but also the location toward which the tip of the needle is directed can be constantly grasped even in the case where the paracentetic needle 100 is bent in the midway to be inserted thereinto (refer to FIG. 6B and 6C).

Figure 7:
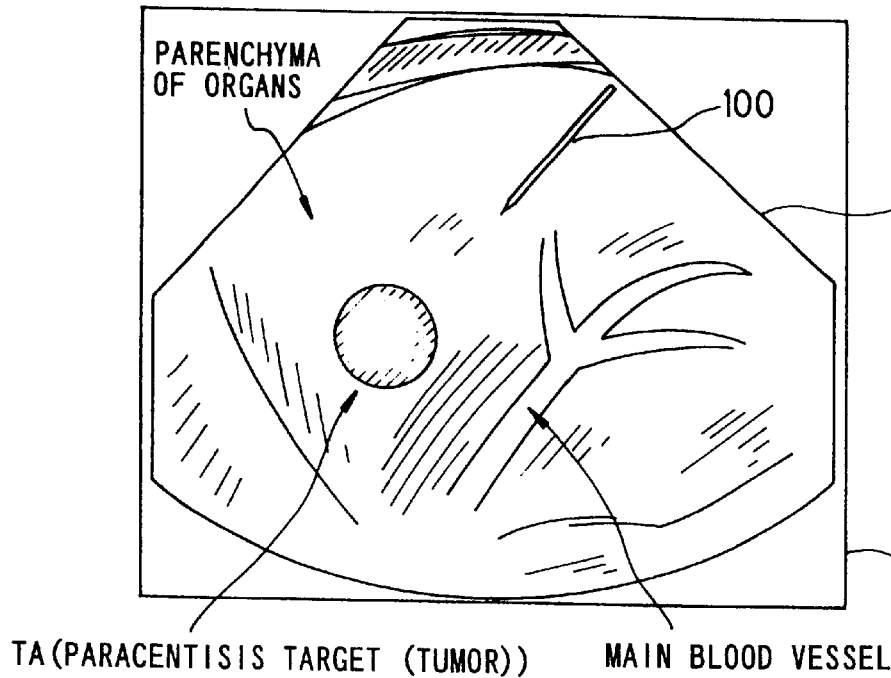
FIG. 7 is an outline view for explaining an example of a monitor display of the two-dimensional tomographic image.

The position information on the tomographic layer CS which is set by the aforementioned processor 17 is input into the display processor 20 as a parameter of the 3D image display condition under the control of the host CPU 19 with the result that, for example, as shown in FIG. 7, a two-dimensional tomographic image IM1 which follows the tomographic image surface CS is displayed on the monitor 7 in real time.

On the two dimensional tomographic image IM1 which is displayed on this monitor 7, the state of the tip of the paracentetic needle 100 which travels toward the target (tumor in the example shown in FIG. 7) TA as well as toward the organs inside the object and the main blood vessels, and the state of the travel direction thereof is displayed on the most appropriate tomographic layer CS. Since this tomographic layer CS can be variably set in real time in such a manner that the tomographic layer CS includes a straight line connecting the tip of the needle 100 with the insertion point by the aforementioned processing for tracing the tip of the needle and processing for setting the cross section even in the case where the paracentetic needle 100 is bent in the midway to change the course of the travel, the operator is capable of navigating the paracentetic needle 100 toward the target TA while confirming the tip of the needle 100 and the travel direction thereof without losing sight of the paracentetic needle 100 on the two-dimensional tomographic image IM1 on the monitor 3.

Consequently, according to this embodiment, the needle 100 can be inserted while confirming on a three-dimensional 3D image the position relation between the position of the tip of the needle 100 and the lesion which constitutes a paracentisis target with the result that more safe and accurate paracentisis can be executed.

Incidentally, other signal processing methods or image processing methods can be applied as well as the cross correlation method when it is possible to trace a track of the movement of the tip of the needle by scanning in three volumes a region which covers the scope of the inside of the object where the paracentetic needle 100 is inserted by using the echo signal from the paracentetic needle 100.

Next, other examples of the tracing processing of the paracentetic needle 100 by the application processor 17 are shown in FIGS. 8 to 11.

Figure 8A:
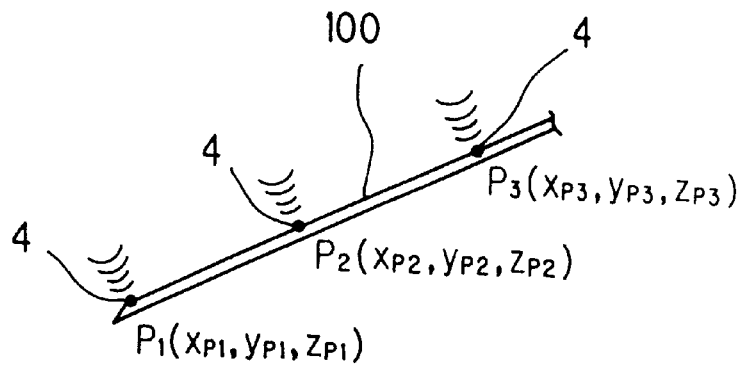
FIGS. 8A to 8B are views for explaining a processing for tracing the whole needle using a plurality of transmitters.
Figure 8B:
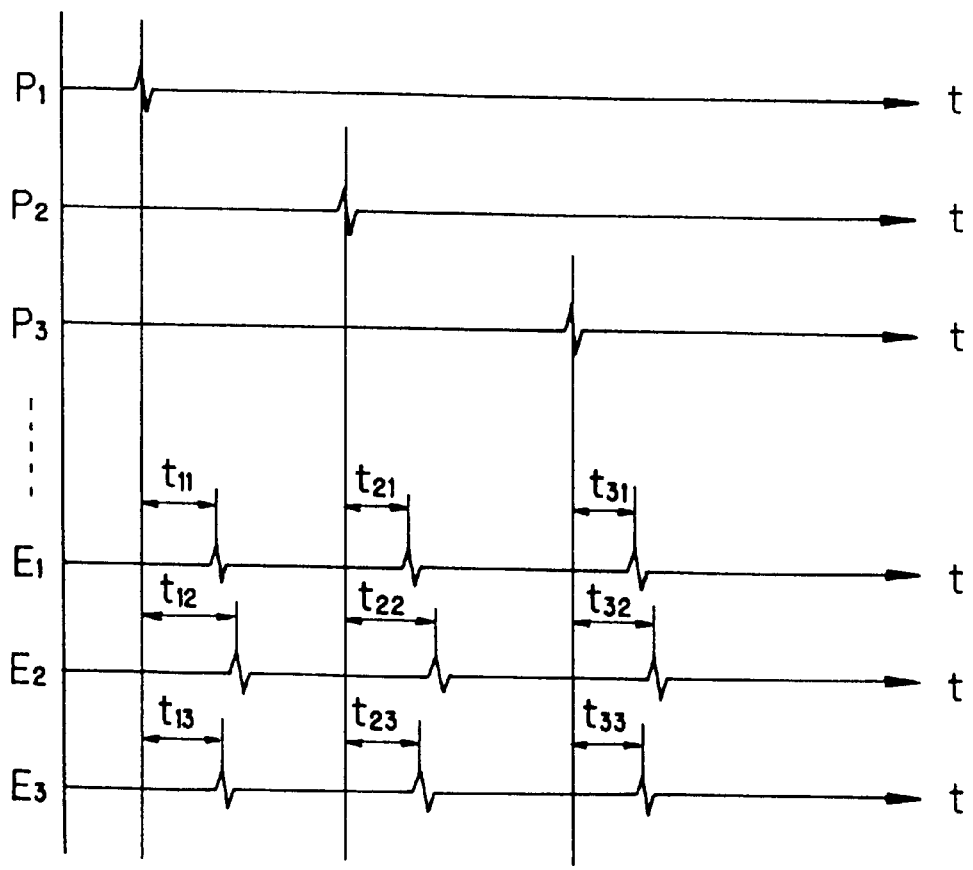

FIGS. 8A and 8B are views for explaining a processing for tracing not only the tip position P of the paracentetic needle 100 but also the position which covers at least part (including the whole) of the tip position thereof.

In this tracing processing, the transmitter 4 which is the same as described above is individually set on each of the plurality of locations P1, P2, P3, ..., Pn different from each other on at least part of the position of the paracentetic needle 100 as shown in FIG. 8A with the result that signals transmitted from each of the transmitters 4 ... 4 at a mutually different timing or with different signal waveforms which can be mutually recognized are received with three or more two-dimensional array probe transducers E1, E2 and E3 located at mutually different locations in the same manner as described above with the result that the algorithm which is the same as described above is executed from the difference in the signal arrival times up to each of the elements E1, E2 and E3 to infer the three-dimensional positions P1, P2 and P3 of each of the transmitters.

For example, in the case of P1 (xP1, yP1, zP1), the position coordinates P1 can be determined when the signal arrival times t1, t2 and t3 up to the transducers E1 (x1, y1, 0), E2(x2, y2, 0) and E3(x3, y3, 0) are measured and the simultaneous equation is solved which is the same as the aforementioned mathematical expression 1. In the same manner, in the case of P2(xP2, yP2, zP2), the position coordinates can be determined by measuring t21, t22, and t23 respectively. On the other hand, in the case of P3(xP3, yP3, zP3) the position coordinates can be determined by measuring t31, t32 and t33 respectively. In the same manner, the position coordinates after P4 are determined. By the interpolation between respective points P1, P2, ..., Pn by using, for example, a spline function, not only the tip of the needle but also the three-dimensional position which covers at least part of the tip thereof can be inferred.

Figure 9A:
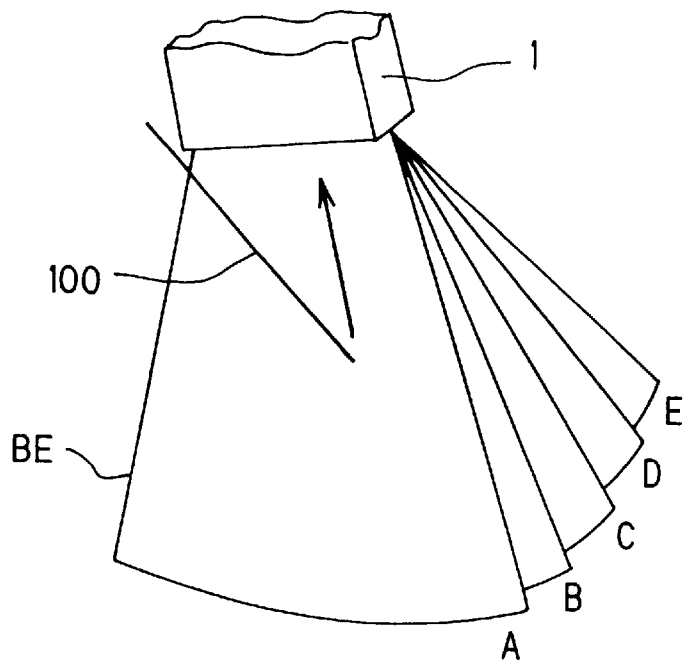
FIGS. 9A and 9B are a view for explaining a processing for inferring the position of the needle on the basis of the strength of the echo signal.
Figure 9B:
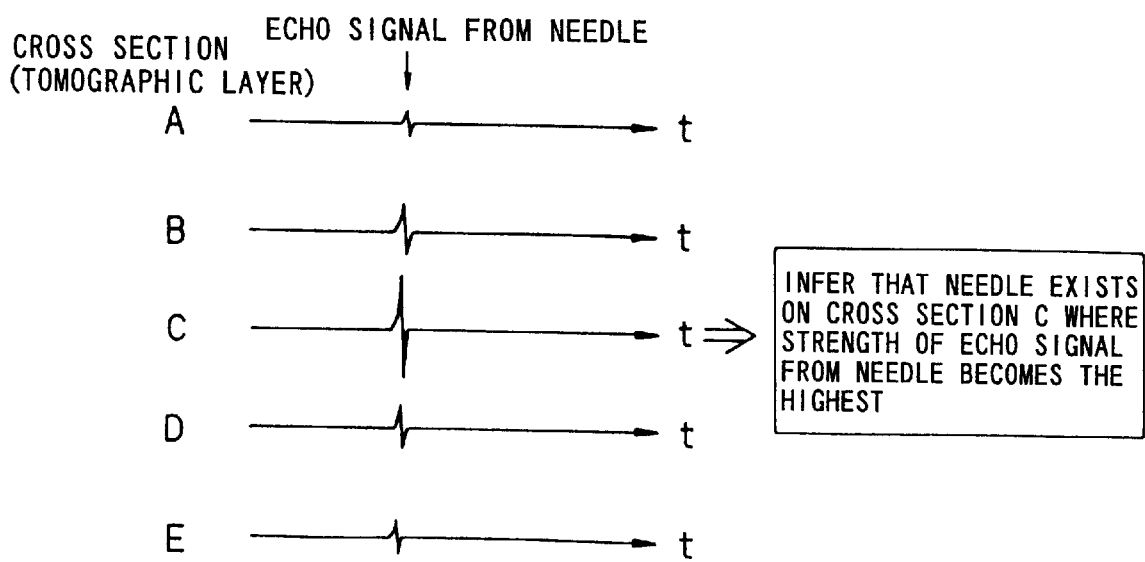

FIGS. 9A and 9B are views for explaining a processing for inferring the position of the paracentetic needle 100 on the basis of the strength of the echo signal from the needle. In this processing for inferring the position of the needle, as shown in FIG. 9A, it is possible to infer the position of the needle by scanning in three volumes the ultrasonic beams BE from the two-dimensional array probe 1 with respect to a region which can cover the scope of the inside of the object where the paracentetic needle 100 is inserted and by examining one after another the condition under which the echo signal strength becomes the highest from the paracentetic needle 100 within the ultrasonic echo signal, for example, the strength of the echo signal for each of the plurality of the cross sections A to E constituting the three volume scan as shown in FIG. 9B. In the case of FIG. 9B, since the cross section which satisfies the condition under which the echo signal becomes the highest is C, it is possible to infer that the paracentetic needle 100 exists on this cross section C.

Figure 10A:
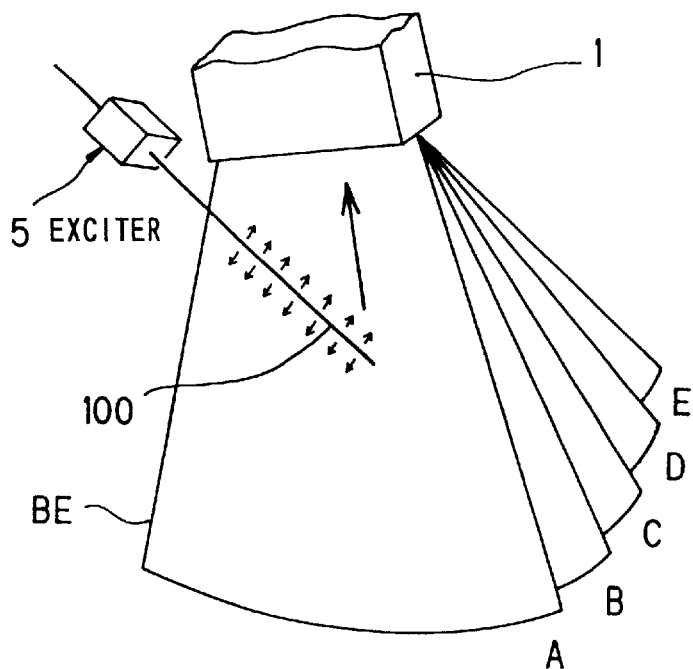
FIGS. 10A and 10B are a view for explaining a processing for inferring the position of the needle on the basis of the power of a Doppler signal.
Figure 10B:
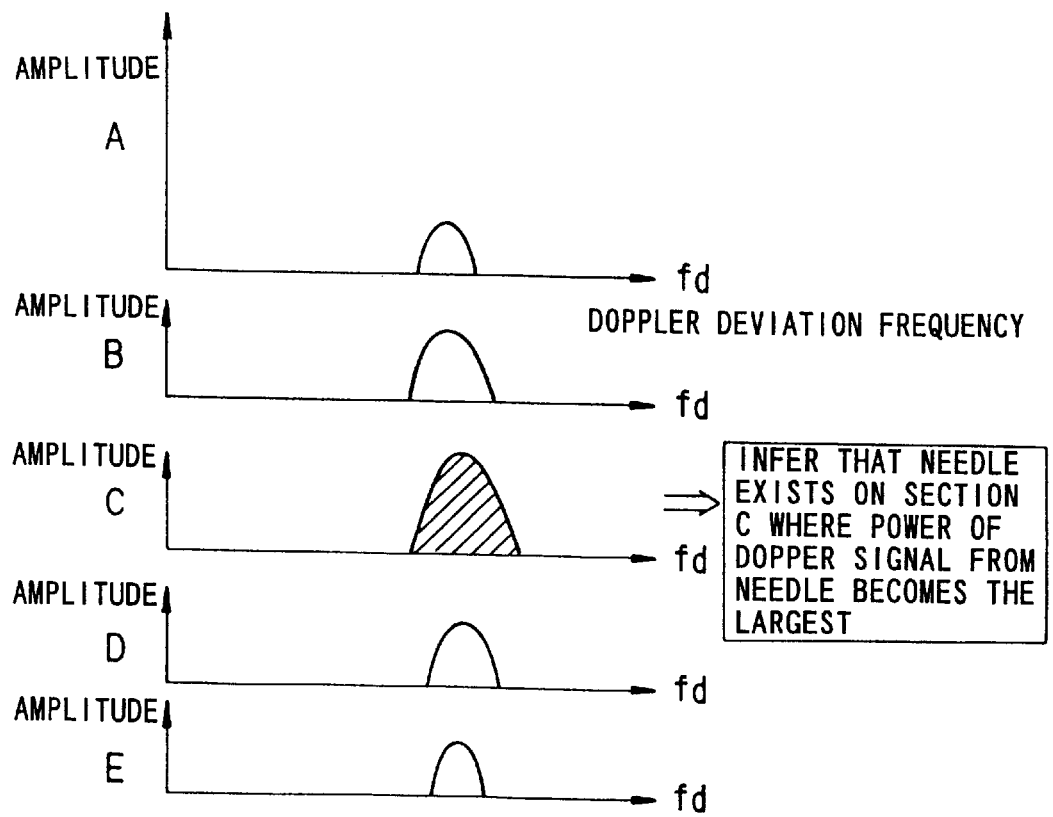

FIGS. 10A and 10B are views for explaining a processing for inferring the position of the paracentetic needle 100 on the basis of the power of the Doppler signal. In this processing for inferring the position of the needle 100, an exciter 5 shown in FIG. 1 is attached as a mechanism for giving a minute vibration to the paracentetic needle 100 as shown in FIG. 10A. It is possible to infer the position of the paracenteic needle 100 by scanning in three volumes the ultrasonic beams BE from the two-dimensional array probe 1 with respect to the region which can cover the scope of the inside of the object where at least the paracentetic needle 100 is inserted while giving a minute vibration to the paracentetic needle 100 by the drive of this exciter 5, and by examining one after another the condition under which the power of the Doppler signal becomes the highest, for example, as shown in FIG. 10B, the power of the Doppler signal for each of the plurality of the cross sections A to E constituting the three volume scan. In the case of FIG. 10B, since the cross section which satisfies the condition under which the power of the Doppler signal becomes the highest is C, it is possible to infer that the paracentetic needle 100 is present on this cross section C.

Figure 11:
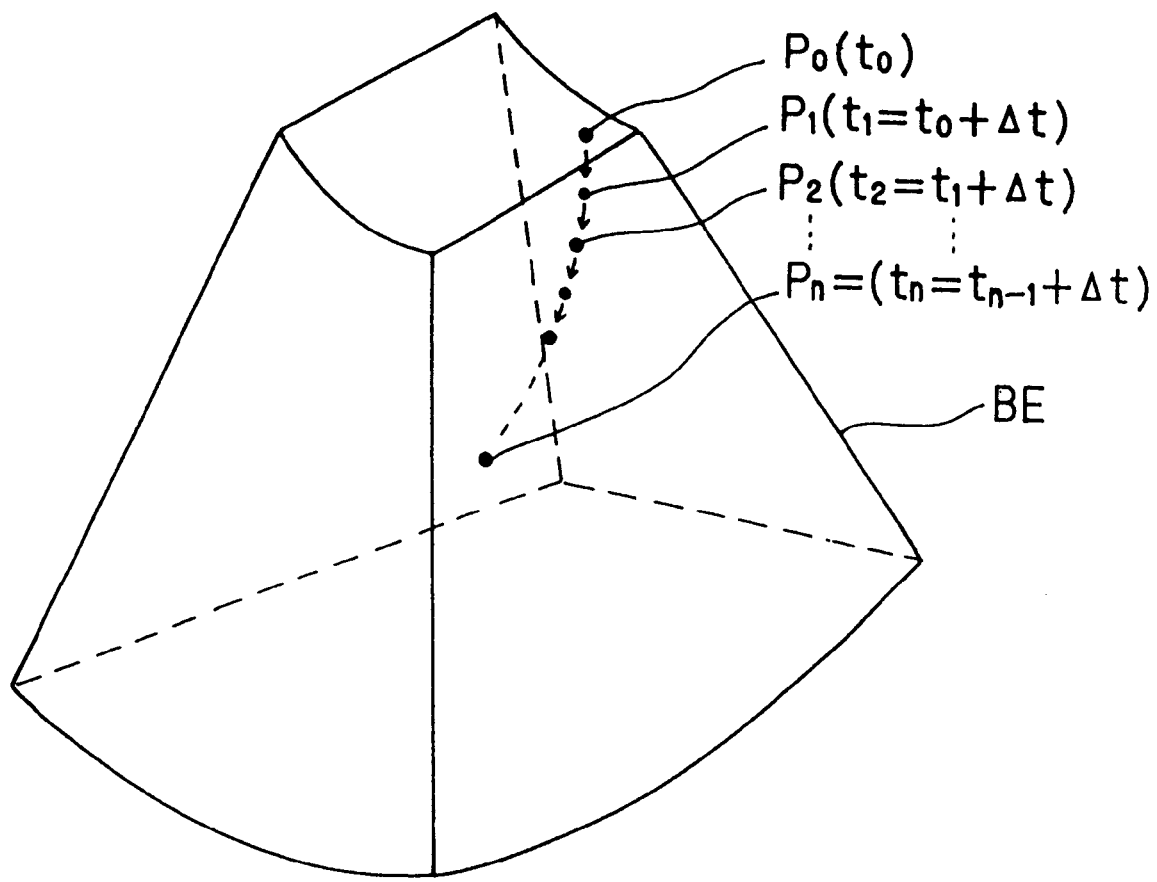
FIG. 11 is an outline view for explaining a processing for tracing the track of the needle tip using a cross correlation method.
Figure 12A:
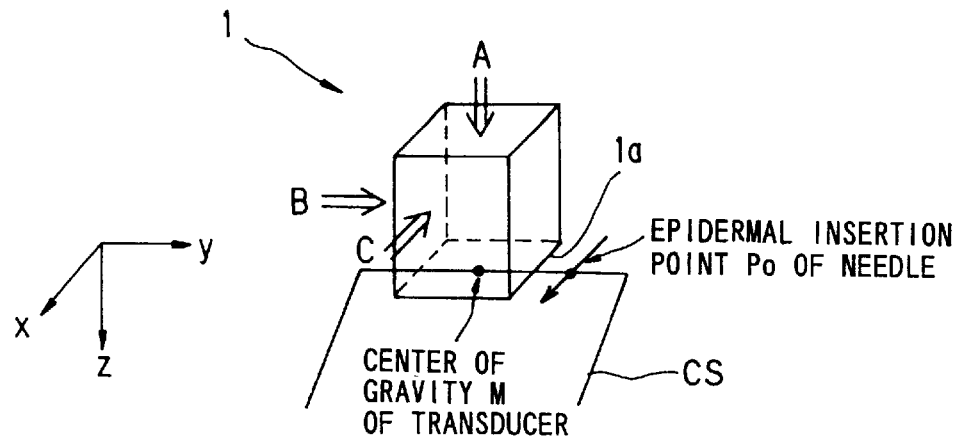
Figure 12C:
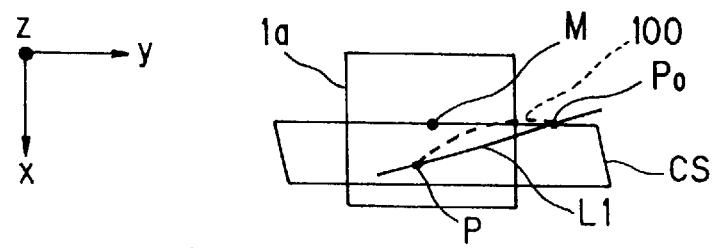
Figure 12C:
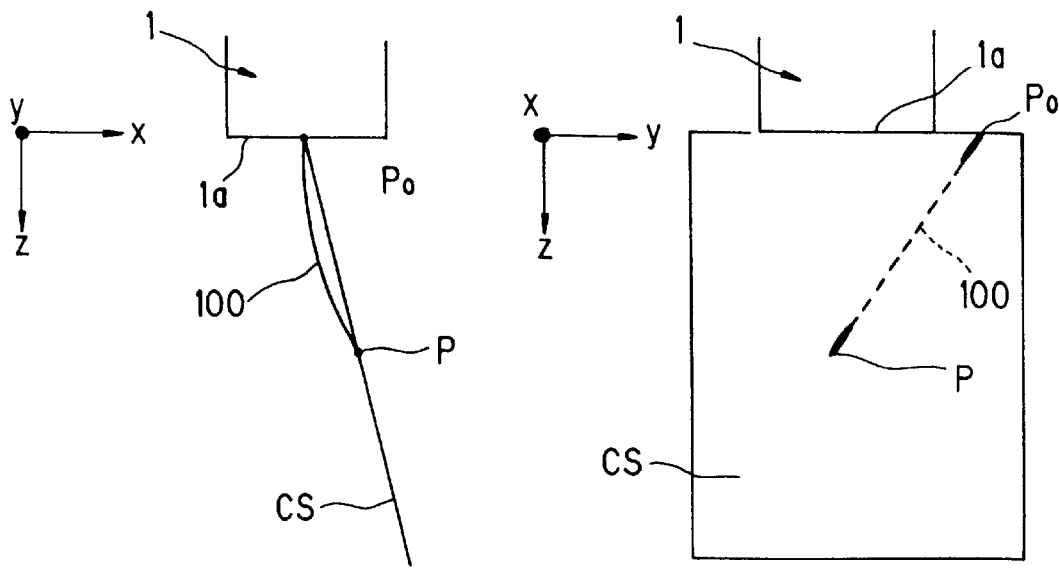
Figure 12D:
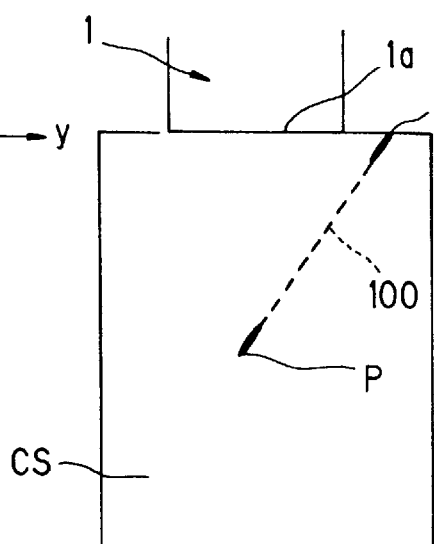
Figure 14A:
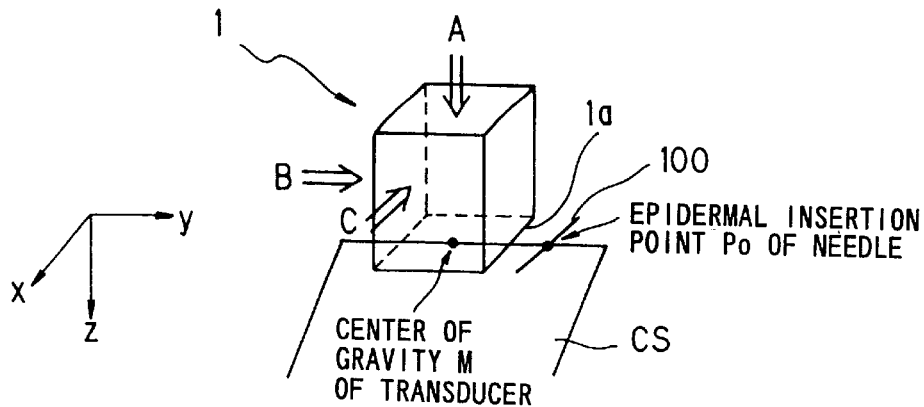
Figure 14C:
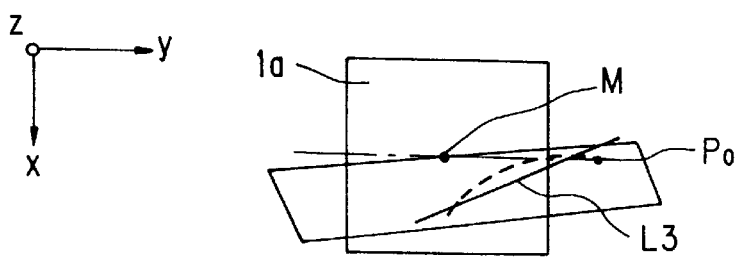
Figure 14C:
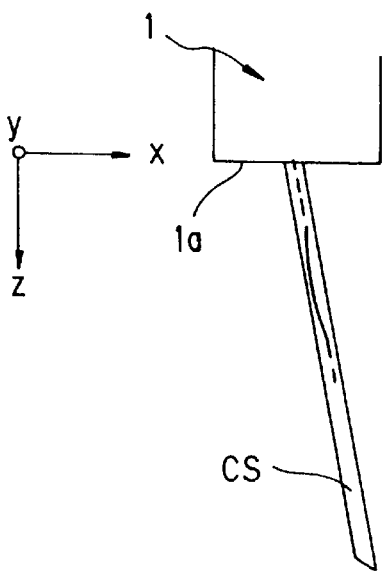
Figure 14D:
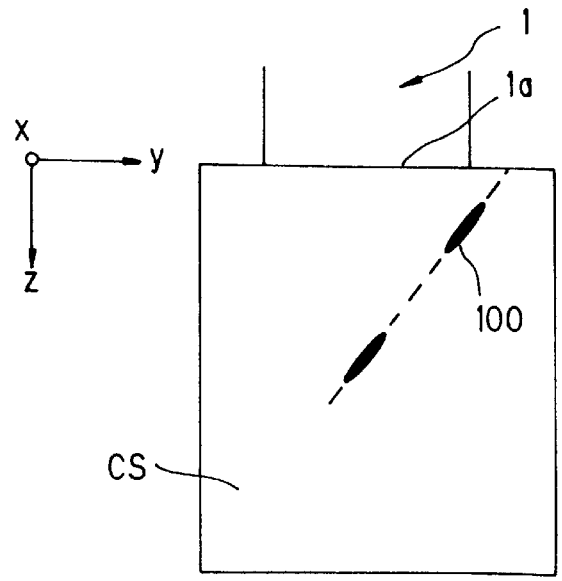

FIG. 11 is a view for explaining a method for tracing the movement of the tip of the paracentetic needle by using the cross correlation method. In this method, when, at first, the paracentetic adapter 101 is attached on the two-dimensional array probe 1 and the position relation between the insertion point of the paracentetic needle into the object and the probe 1 is fixed, the position where the tip of the paracentsis needle 100 appears at first inside of the three volume scan of the ultrasonic beams BE is defined in one sense. This position is denoted by P0 while the time is denoted by to. Subsequently, on the basis of the echo signal from the point P0 at time t0 the tip position of the needle at time t=t0Δt is inferred by means of the cross correlation method. The point is denoted by P1. Hereinbelow, in the same manner, the tip positions P2, P3, . . . , Pn of the needle 100 at times t2, t3, . . . , tn are inferred one after another. By executing the algorithm using such cross correlation method with the application processor 17, it becomes possible to trace the track of the movement of the tip of the paracentetic needle 100.

Incidentally, other signal processing methods or image processing methods can be applied as well as the cross correlation method when it is possible to trace a track of the movement of the tip of the needle by scanning in three volumes a region which covers the scope of the inside of the object where the paracentetic needle 100 is inserted by using the echo signal from the paracentsis needle 100.

Next, other examples of the processing for setting the cross section CS of the two-dimensional tomographic image IM1 by the application processor 17 are shown in FIGS. 12 to 15 respectively.

The processing for setting the cross section shown in FIGS. 12A to 12D is intended to set on the cross section CS of the two tomographic image a surface including the three points, namely, the epidermal insertion point P0 of the paracentetic needle 100, the Up position P thereof, and the reference point which is regulated in advance, namely, the center of gravity (center) M of the transducer surface in the two-dimensional array probe 1. In this case, the two-dimensional tomographic image can be displayed on the cross section which is most appropriate for recognizing the position relation between the direction in which the tip of the needle is directed and the paracentisis target TA in the same manner as described above. Incidentally, the reference point may be located on other positions in addition to the center of gravity of the transducer surface.

The processing for setting the cross section shown in FIGS. 13A to 13D is intended to sample the tip position of the needle P at a definite time interval by the processing for tracing the aforementioned paracentetic needle 100 to determine the position coordinates point, thereby setting on the cross section CS of the two-dimensional tomographic image on the basis of a surface which passes through a straight line recursion line L2 obtained from the position coordinates point and a normal line (a z axis shown in the drawings) which is vertical with respect to the surface 1a of the transducer of the two-dimensional array probe 1. In this case, too, the two-dimensional tomographic image IM1 can be displayed on the cross section which is most appropriate for recognizing the position relation between the direction in which the tip of the paracentetic needle 100 is directed and the paracentetic target TA.

The processing for setting the cross section shown in FIGS. 14A to 14D is intended to sample the tip position of the needle P at a definite time interval by the processing for trading the aforementioned paracentetic needle 100 to determine the position coordinates point, thereby setting on the cross section CS of the two-dimensional tomographic image on the basis of a surface which passes through the straight line recursion line 12 obtained from the position coordinates point and the reference point which is regulated in advance, namely, the center of gravity (center) M of the surface 1a of the transducer of the two-dimensional array probe 1. In this case, too, in the same manner as described above, it is possible to display the two-dimensional tomographic image IM1 on a cross section which is most appropriate for recognizing the position relation between the direction in which the tip of the paracentetic needle 100 is directed and the paracentetic target TA. Incidentally, the reference point may be other locations than the center of gravity of the surface of the transducer.

Figure 15A:
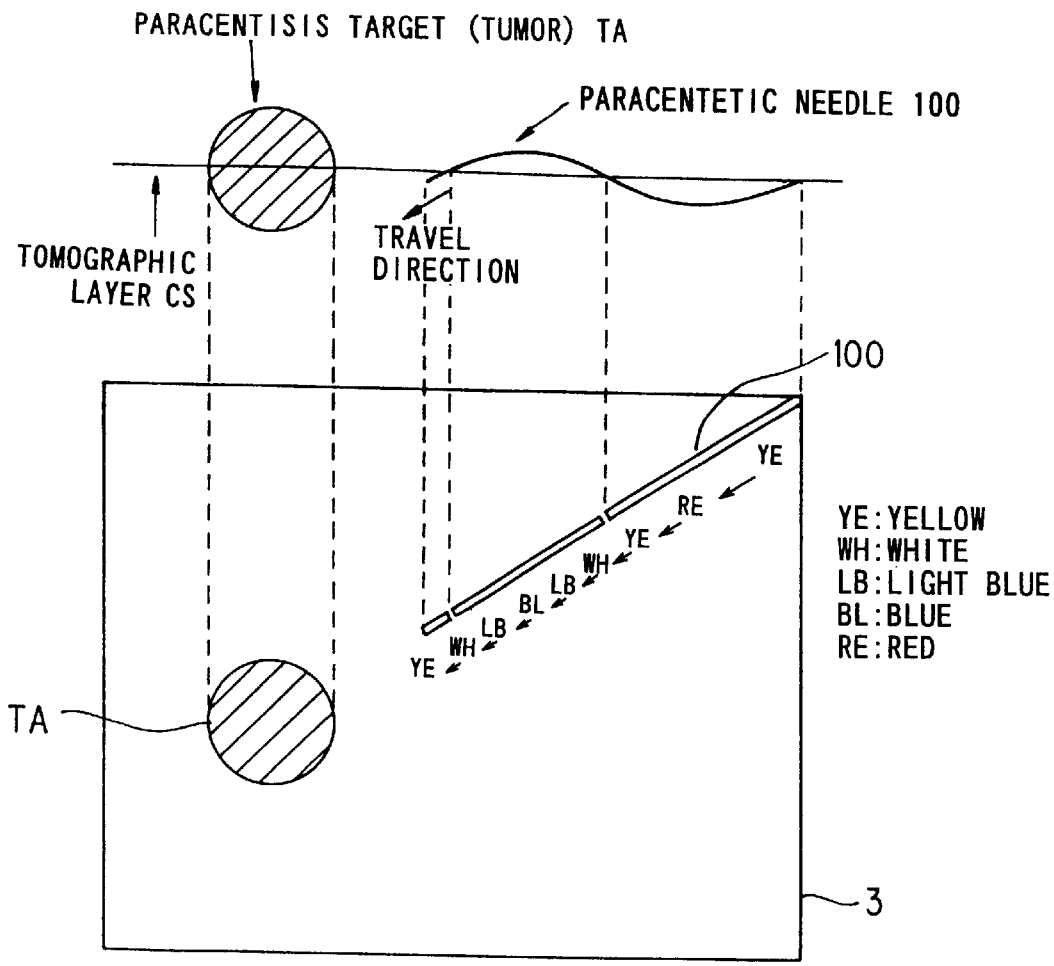
FIGS. 15A and 15B are views for explaining a display example in which the position of the paracentetic needle with respect to the cross section position of the two-dimensional tomographic layer can be visibly recognized.
Figure 15B:
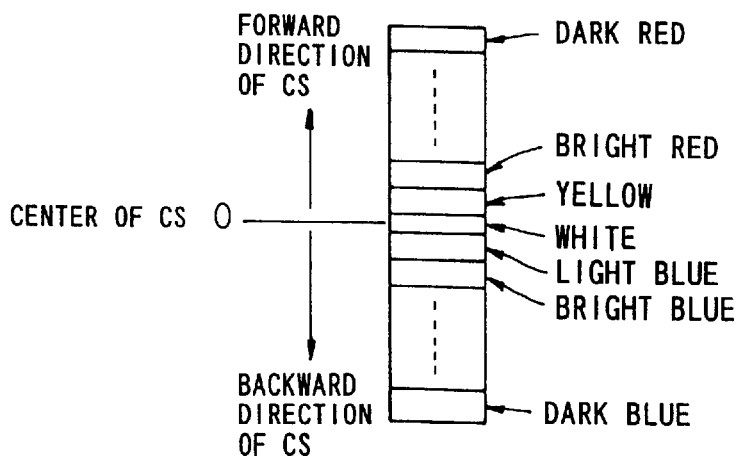

FIGS. 15A and 15B are views for explaining a processing for displaying an image which enables recognition of the state of the travel of the paracentetic needle 100 which is in a bent state without changing in real time the cross section CS of the two-dimensional tomographic image Im1 which is set in advance to grasp the lesion which is a target TA inside of the object. In this image display processing, the position (at least part thereof) of the paracentetic needle 100 which is traced as described as shown in FIG. 15A is displayed so that the position can be visibly recognized on the screen as to whether the position of the needle is located before or at the rear side of the cross section CS sandwiching the position of the cross section CS. In this example, there is shown a method for changing at least one of the color and the luminance of the paracentetic needle 100 which is displayed on the two-dimensional tomographic image. In this case, it will be more effective when the hue and the gray scale of the luminance corresponding to the spaced apart distance is set in advance so as to enable a visible recognition of how much the position of the needle is separated from the cross section particularly as shown in FIG. 15B.

Next, as another processing for controlling the image display by the application processor 17, the processing with respect to the display control of the three-dimensional projection image will be shown in FIGS. 16 through 25.

Figure 16:
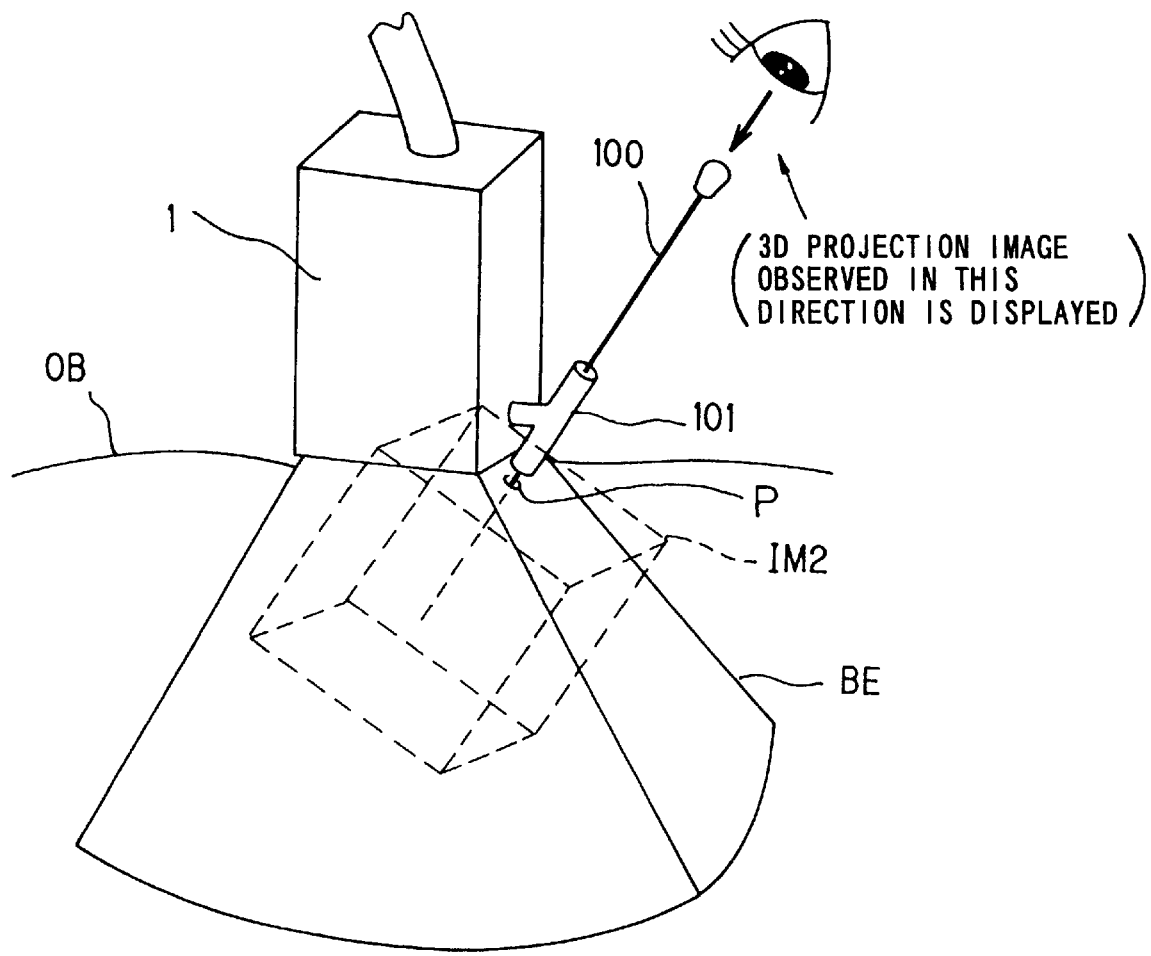
FIG. 16 is a concept view for explaining a display example of a three-dimensional projection image.

FIG. 16 is a view for explaining the 3D image (three-dimensional projection image) IM2 in which the tip of the needle travels from the epidermal insertion point P of the paracentetic needle 100. In this case, the paracentetic adapter 101 is attached and fixed on the two-dimensional array probe 1, and the direction in which the paracentetic needle 100 is guided is definite with respect to the two-dimensional array probe 1. Consequently, the 3D image IM12 can be displayed on the monitor by controlling the display processor 20 in such a manner that the application processor 17 reconstitutes the 3D volume data on the basis of the direction in which the paracentetic needle 100 is guided.

Figure 17A:
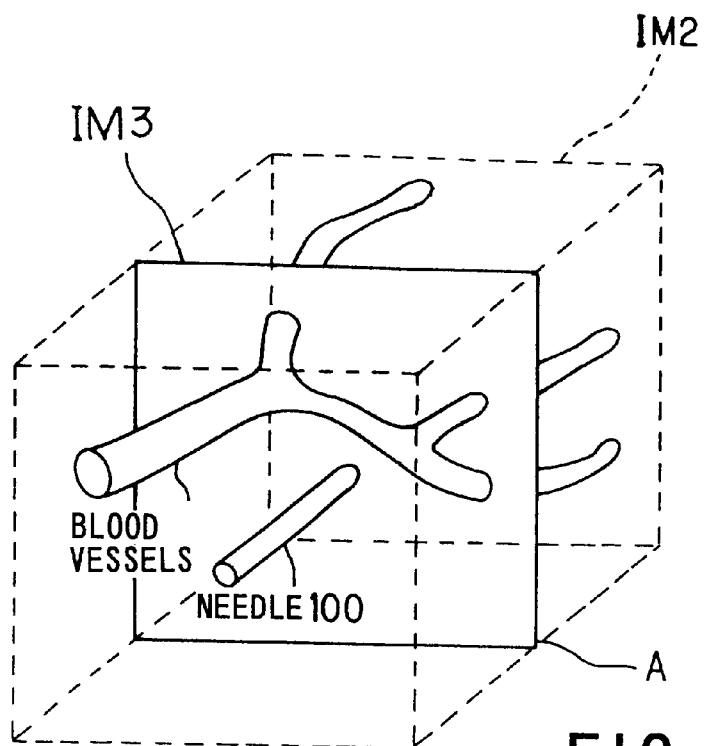
FIGS. 17A and 17B are outline views for explaining a display example of the tomographic image in the three-dimensional projection image.
Figure 17B:
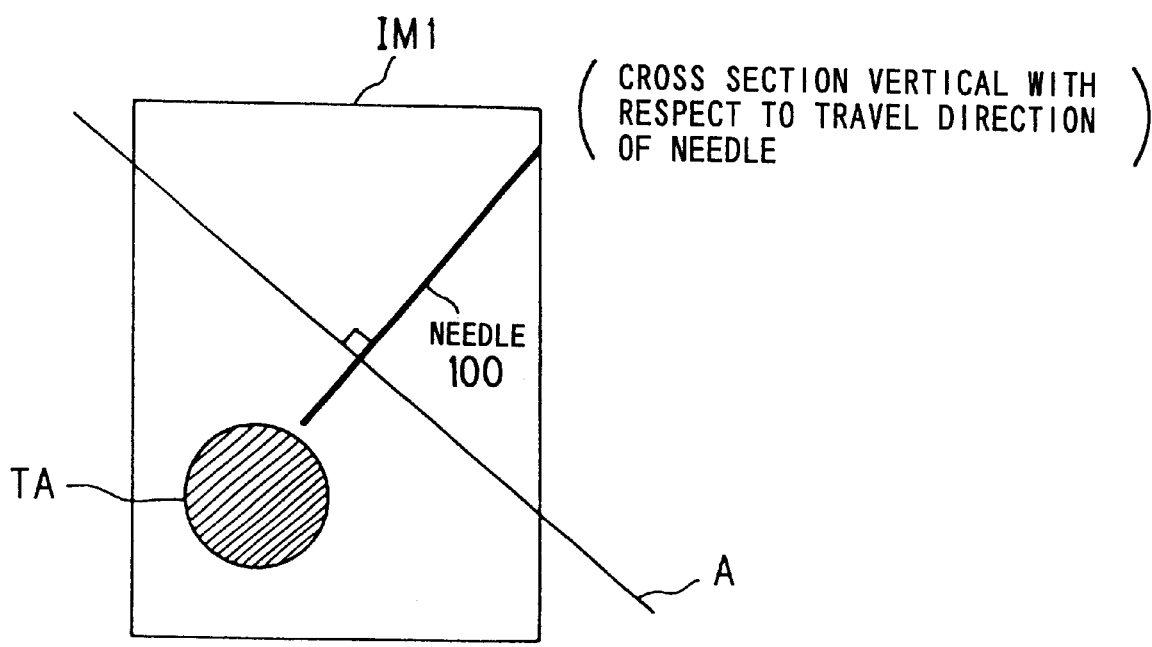

FIGS. 17A and 17B are views for explaining an example of a method for displaying a state in which this 3D image IM2 incorporates therein a tomographic image IM3 of a surface A which is vertical with respect to the direction in which the paracentetic needle 100 travels. FIG. 1 7A shows an example of the 3D image IM2 which covers a region including blood vessels inside of the object and the paracentetic needle 100, and a tomographic image IM3 of the surface A vertical with respect to the progression direction of the needle 100 which surface is displayed in a state in which the surface 1A is incorporated in this 3D image IM2. FIG. 17B shows the position of the tomographic image IM3 of the surface A which is observed on the two-dimensional tomographic image IM2 of the cross section set in the aforementioned processing for setting the cross section. It is possible to display this two-dimensional tomographic image IM1 and the 3D image IM2 at the same time on the monitor 3. As a consequence, it becomes possible to navigate the paracentetic needle 100 while observing an image which is more excellent in visibility.

Figure 18A:
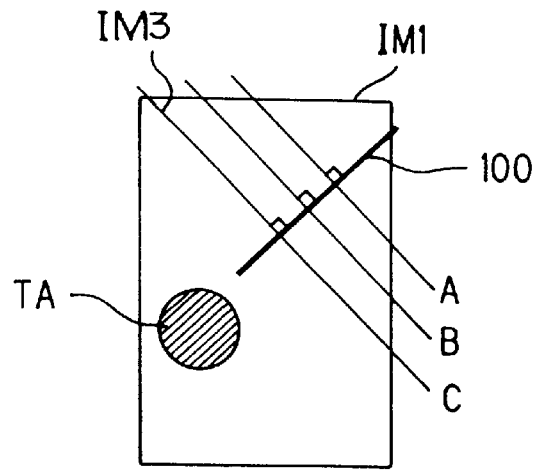
FIGS. 18A and 18B are outline views for explaining in which the cross section of the tomographic image within the three-dimensional projection image is arbitrarily selected.
Figure 18B:
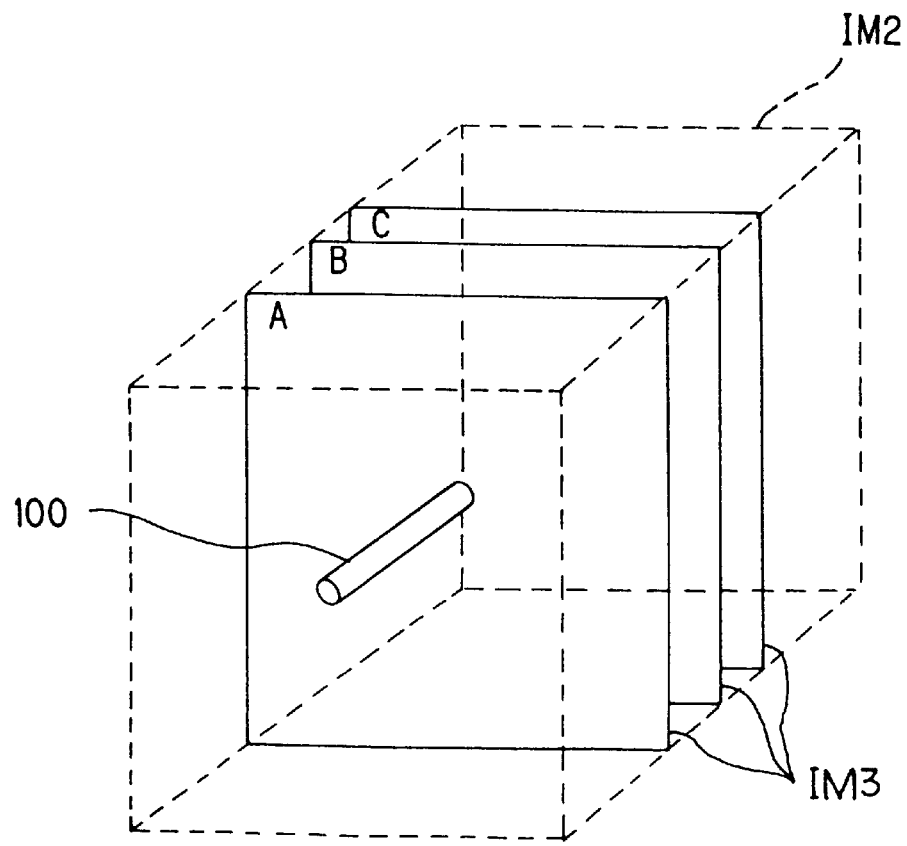

FIGS. 18A and 18B are views for explaining one example of a method for selecting the tomographic image IM3 of the surface A vertical with respect to the paracentetic needle 100 shown in FIG. 17. In this case, the tomographic image IM3 of the selected surface is incorporated into the 3D image IM2 shown in FIG. 18B when the operator arbitrarily selects a plurality of surfaces A, B and C vertical with respect to the axis along the axis of the direction in which the paracentetic needle 100 travels on the two-dimensional tomographic image 1 Ml shown in FIG. 18A.

Figure 19A:
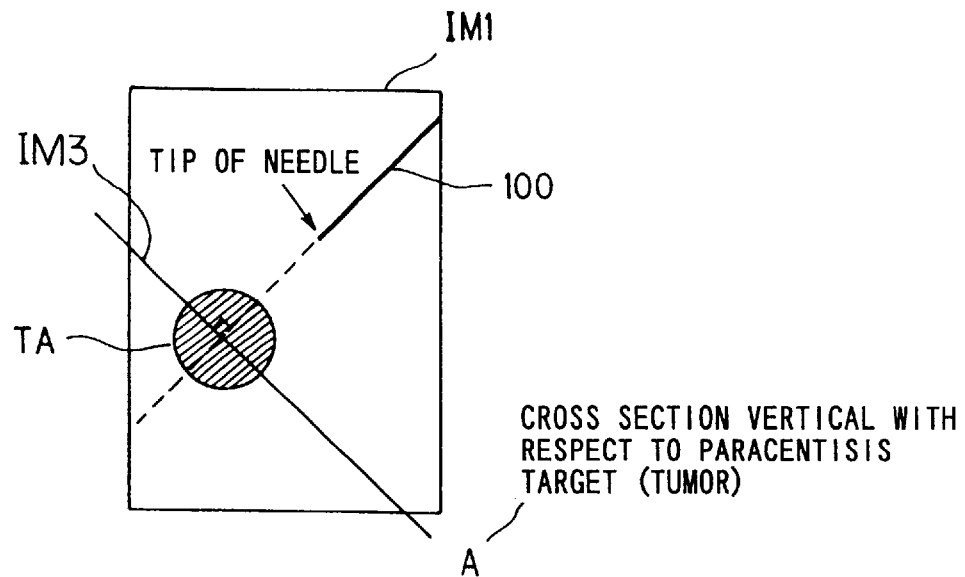
FIGS. 19A to 19B are outline views for explaining the setting of the cross section of the tomographic image which passes through a target and a display example thereof.
Figure 19B:
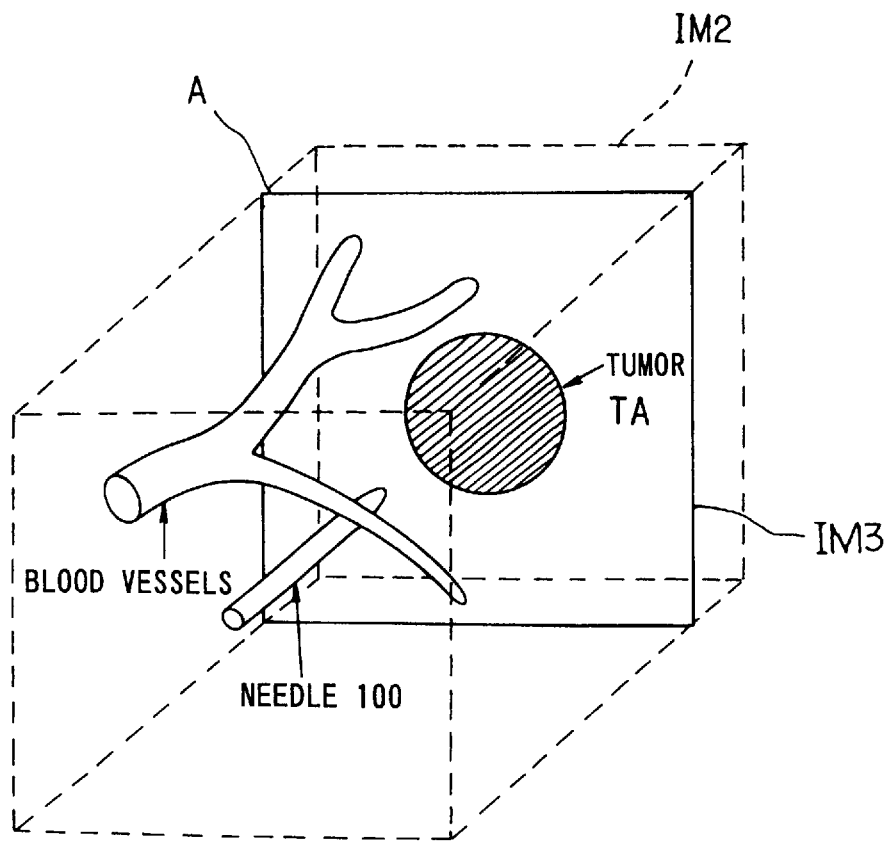
Figures 20A, 20B, 20C:
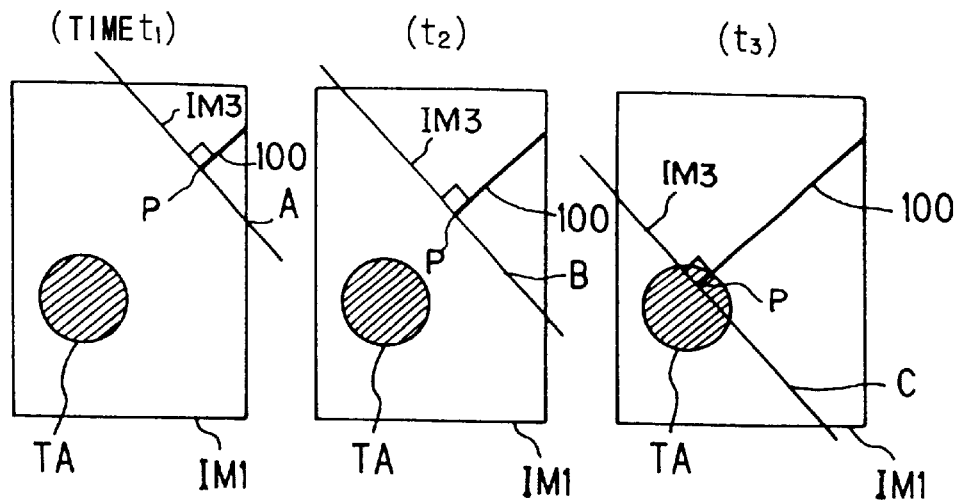
FIGS. 20A to 20D are outline views for explaining the setting of a cross section which passes through the position of the tip of the needle which changes at each moment and a display example thereof.
Figure 20D:
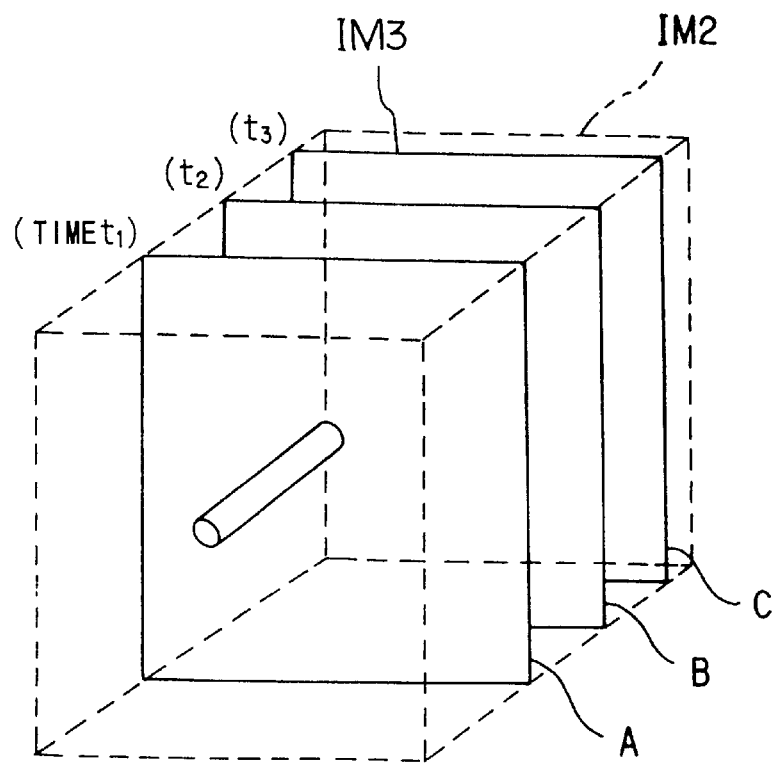

FIG. 19A and 19B show a display example in the case where the position of the tomographic image IM3 in the 3D image IM2 shown in FIGS. 17 and 18 is set on a surface which is vertical with respect to the direction in which the paracentetic needle travels and which passes through the target TA. In this case, it is possible to navigate the paracentetic needle in the state in which the target TA is constantly caught within the 3D image IM2.

FIGS. 20A through 20D show one example of a method for displaying the tomographic image IM3 on the surface A passing through the tip position of the needle following the movement of the needle. In this case, the vertical surface A passing through the tip position P (refer to FIG. 20A, 20B and 20C) of the paracentetic needle at times t1, t2 and t3 is variably set following the movement of the tip of the needle, and the tomographic image IM3 of the surface A is displayed (refer to FIG. 20D).

Figure 21:
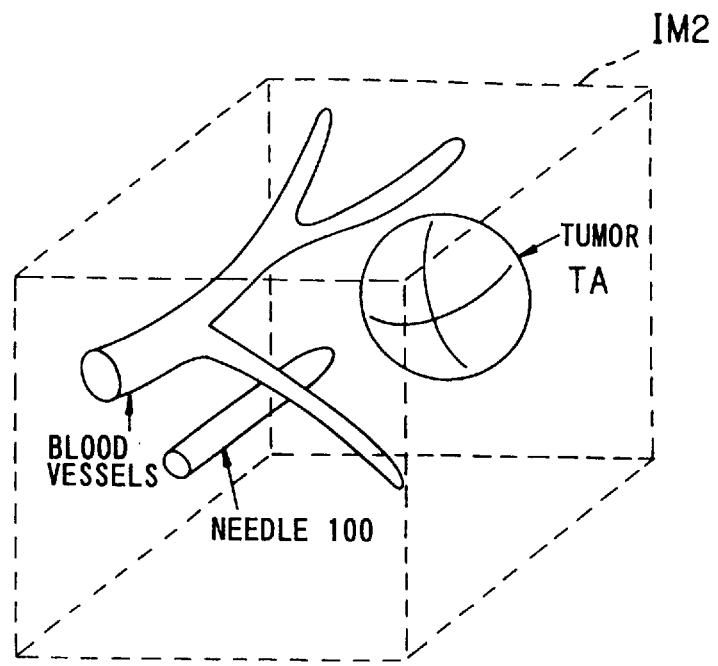
FIG. 21 is an outline view for explaining a display example of the three-dimensional projection image which covers blood vessels, the target (tumor) and the paracentetic needle.

FIG. 21 shows a display example of the 3D image IM2 at the boundary surface which covers a region including the running of blood vessels inside of the object, the lesion which constitutes the target TA, and the paracentetic needle 100.

Figure 22:
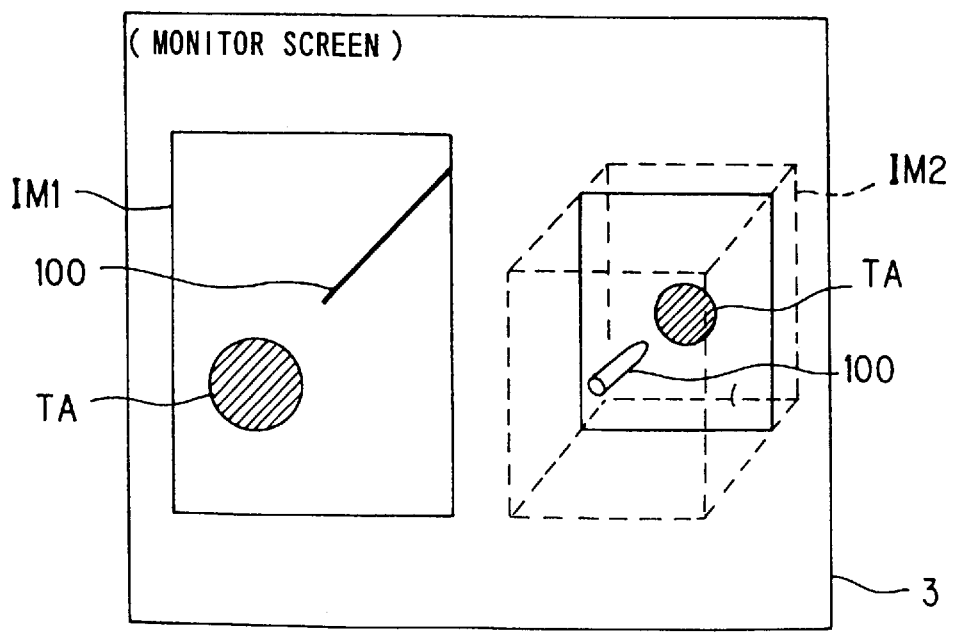
FIG. 22 is an outline view for explaining a display example on which a two-dimensional tomographic image and a three-dimensional projection image are arranged on the same screen.

FIG. 22 shows an example in which the 3D image IM2, the two-dimensional tomographic image IM1 of the cross section which is set in the aforementioned processing for setting the cross section are arranged on the same monitor 3.

Figure 23:
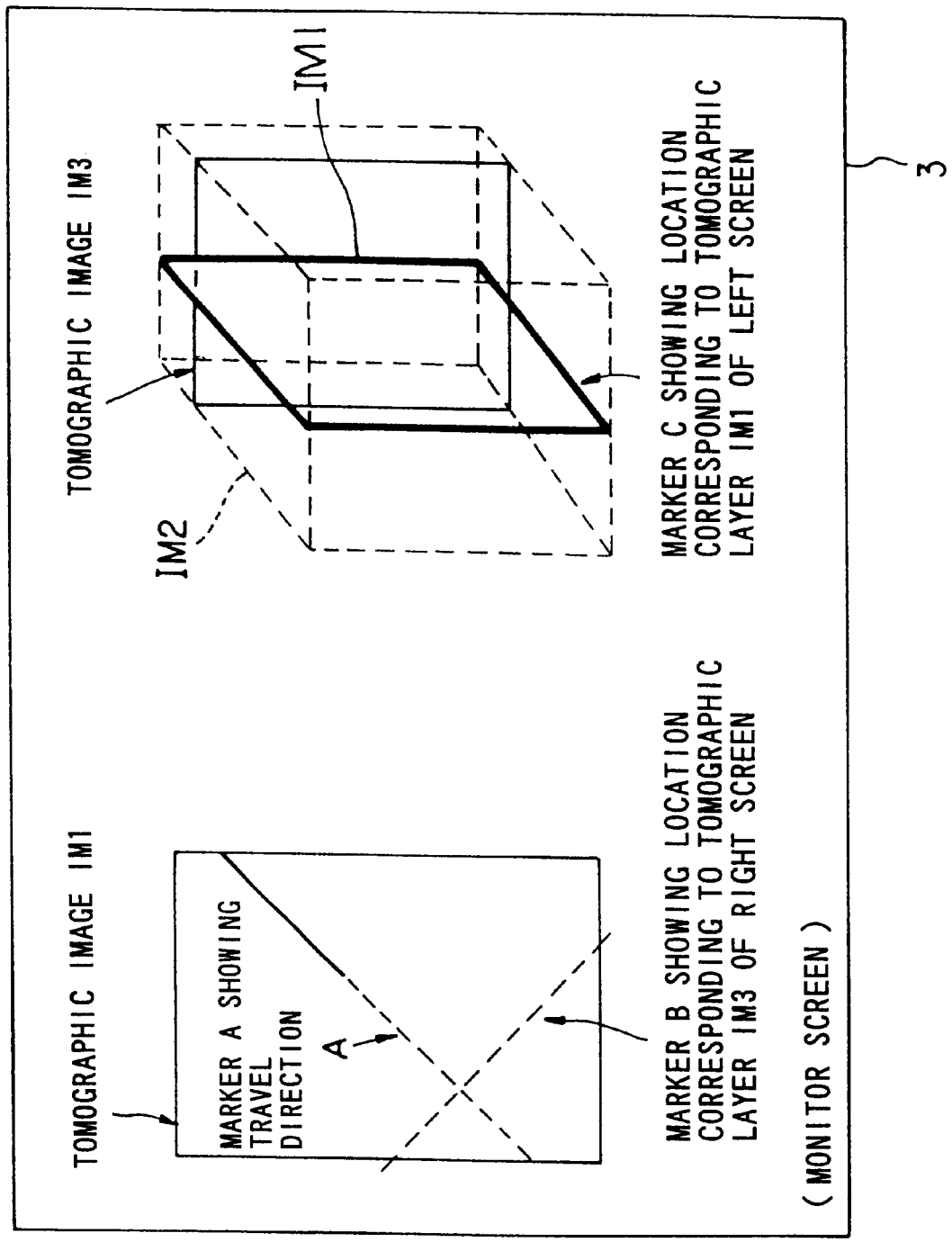
FIG. 23 is an outline view showing a display example of each kind of marker in the two-dimensional tomographic image and the three-dimensional projection image.

Next, an example of a processing for displaying a marker which processing is appropriate for the display of images such as the aforementioned 3D images is shown in FIGS. 23 to 25.

FIG. 23 is a view for explaining an example of the marker display in which the position relation or the like of the mutual cross section can be recognized on the image in the display examples of the images IM1 and IM2 shown in FIG. 22. For example, in the two-dimensional tomographic image IM1, a marker A showing the travel of the needle, a marker B showing the position corresponding to the cross section of the tomographic image IM1 incorporated in the 3D image IM2 can be displayed in the two-dimensional tomographic image IM1, and a marker C showing the position corresponding to the cross section of the two-dimensional tomographic image can be displayed in the 3D image IM2.

Figure 24A:
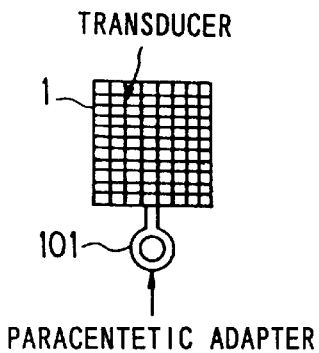
FIGS. 24A to 24D are outline views showing a display example of the marker, the view showing an arrangement position of a needle insertion point and a transducer.
Figure 24B:
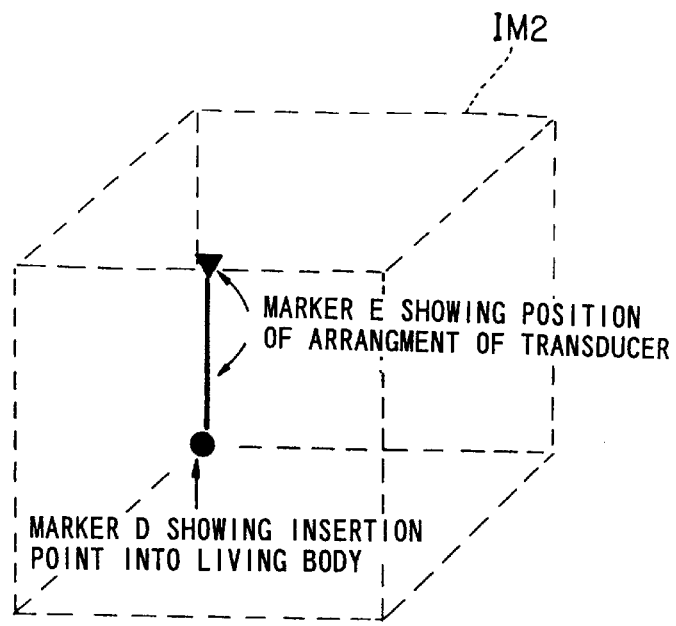
Figure 24C:
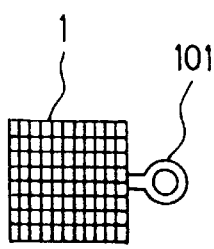
Figure 24D:
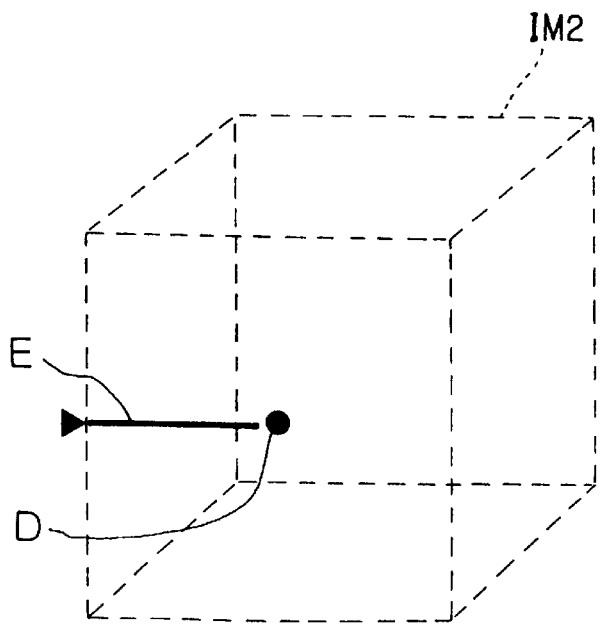

FIGS. 24A to 24B are views for explaining an example of the marker display in which the vertical and the horizontal directions of the 3D image IM2 and the position relation of the object as seen from the epidermis can be grasped on the image. In this case, in the position relation between the arrangement of the transducer and the paracentetic adapter 101 at the time of observing the probe 1 shown in FIGS. 24A and 24C, a marker D showing the epidermal insertion point of the paracentetic needle 100 shown in Figs.24B and 24D and a marker E showing a straight line (for example, corresponding to one of the axes in the two-dimensional arrangement direction of the transducer) connecting the epidermal insertion point with a reference point on the probe 1 which is determined in advance are displayed in the 3D image IM2.

Figure 25A:
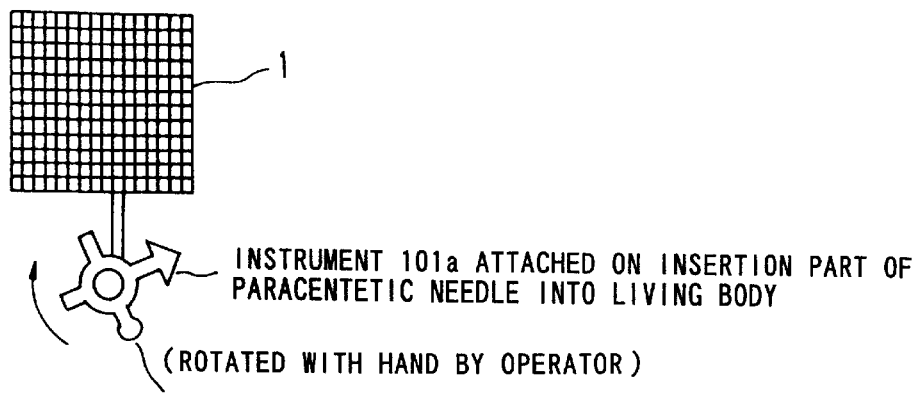
FIG. 25A and 25B are concept views showing a display example of a marker in which the position relation and a direction of images as seen from the epidermis of a object can be recognized.
Figure 25B:
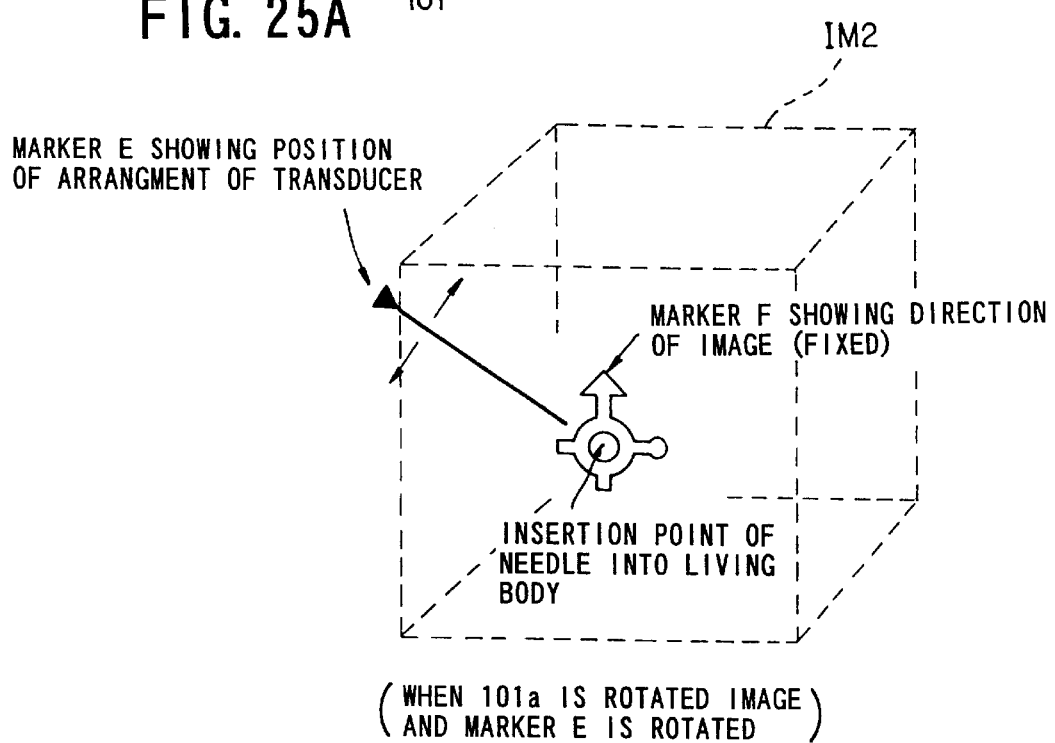

FIGS. 25A and 25B show an example in which an instrument which enables the recognition of the vertical and the horizontal direction (east, west, south and north), for example, a rotatable cross-shaped instrument 101a which becomes a marker of the direction is attached on the side of the insertion operation of the paracentetic needle 100 in the paracentetic adapter 101 so that a marker F taking after the form of the instrument 101a is displayed by allowing the attachment direction of the instrument 101a to correspond to the position relation of the image. In this case, the structure is such that the rotation position information of the cross-shaped instrument 101a can be recognized by the application processor 17 within the system main body via the paracentetic adapter 101. When the cross-shaped instrument 101a is rotated with the hand by the operator as shown in FIG. 25A, the marker F is rotated in accordance with the rotation amount of the instrument and can be displayed as shown in FIG. 25B.

Incidentally, it goes without saying that each of other examples in the aforementioned embodiments can be embodied singly or in an appropriate combination thereof within the scope of the present invention. One example will be explained hereinbelow.

In the beginning, at the time of starting the ultrasonic paracentisis, 3D data including the B mode information and information on the blood flow is obtained by the execution of the three-dimensional volume scan by means of the ultrasonic diagnosis apparatus, the processing (refer to FIGS. 3, 4, 8 through 11) for tracing the paracentetic needle 100 by the application processor 17, and the processing (refer to FIGS. 5, 6, 12 through 15) for setting the most appropriate cross section CS using the result of the tracing processing are performed with the result that the two-dimensional tomographic image IM1 (refer to FIGS. 7, 17B, 18A, 19A, 20A through 20C or the like) based on the B mode 3D information on the most appropriate cross section CS which is set in the aforementioned processing is displayed, for example, on the monitor in real time.

Along with this, the three-dimensional projection image IM1 (refer to FIG. 1 7A and FIG. 21 or the like) of blood vessels, the paraentetic needle, the target or the like is constituted in the case of observing the target (such as tumor, lesion and the like) TA from the paracentetic direction of the paracentetic needle 100 in other 3D image processings by the application processor 17 on the basis of the aforementioned 3D data in another 3D image processing by the application processor 17 on the basis of the aforementioned 3D data (refer to FIG. 16). Then, the projection image is displayed on the monitor at the same time with the aforementioned two-dimensional tomographic image IM1 (refer to FIG. 22).

The 3D image processing in this case includes the processing of synthesizing the 3D image of the paracentetic needle 100 obtained in the aforementioned tracing processing or the like, the 3D image of the blood vessels obtained from the Doppler marker 200 is observed, in the case where the paracentetic needle 100 is bent in the midway, and the direction of the tip of the needle is deviated from the target TA, it is possible to easily find where the tip of the needle attains when the needle is inserted as it is.

Incidentally, in the aforementioned embodiments and other embodiments, the structure is such that the paracentetic adapter 101 for inserting the paracentetic needle 100 is attached on the ultrasonic probe 1 and the direction (angle) for guiding the paracentetic needle 100 is fixed. However, the present invention is not limited thereto. For example, a structure can be adopted in which a rotation mechanism or the like is added in which the angle of the paracentetic adapter 101 can be arbitrarily changed automatically or by the hand with respect to the ultrasonic probe 1 thereby making it possible to change the angle of the paracentetic needle 100 when required. In this case, information on the angle of the paracentetic needle is preferably input to the side of the system main body 2 from the side of the paracentetic adapter 101.

In this case, as shown in FIG. 19B, the 2D tomographic image IM3 on the vertical cross section A passing through the lesion TA is overlapped with and displayed in the 3D projection image IM2 of the paracentetic needle 100 and the blood vessels, or as shown in FIGS. 17 or 18, the 2D tomographic image IM3 on the vertical cross section A passing through the tip part of the paracenteic needle 100 is overlapped with and displayed in the 3D projection image IM2.

Figure 26A:
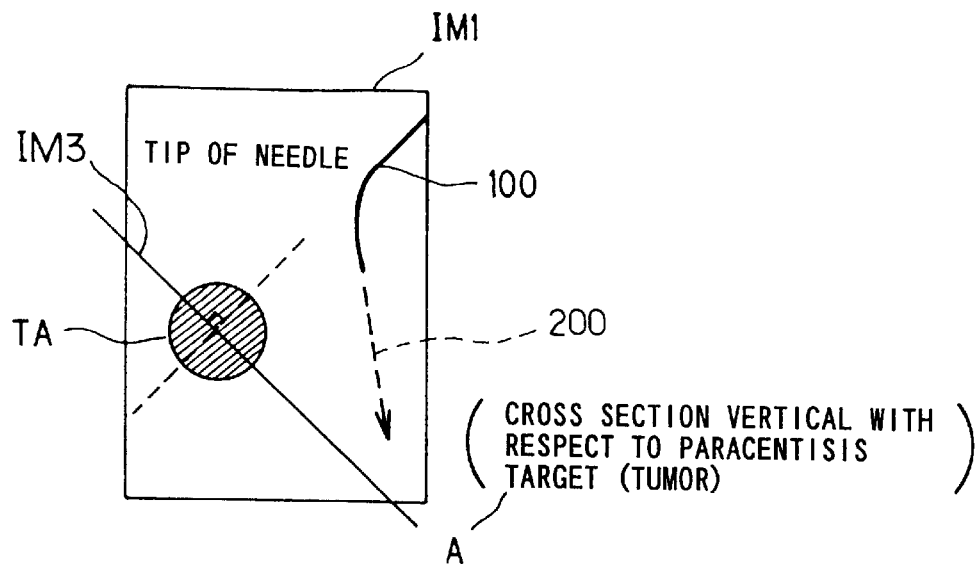
FIGS. 26A and 26B are concept views for explaining a display example of a marker showing a travel direction of the tip of the needle.
Figure 26B:
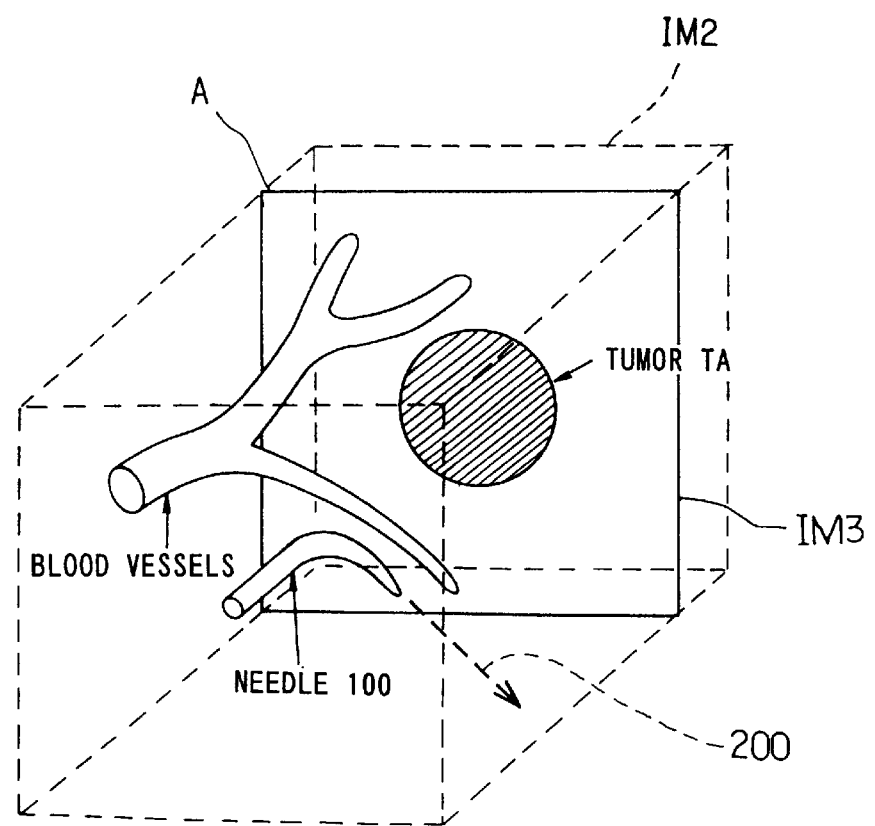

Furthermore, in the form of the aforementioned embodiment or other embodiments, as additional information for navigating the paracentetic needle 100, it is possible to display a marker 200 along a line connecting the tip of the paracentetic needle 100 and the travel direction thereof a shown in FIGS. 26A and 26B. When the marker 200 is observed, in the case where the paracentetic needle 100 is bent in the midway, and the direction of the tip of the needle is deviated from the target TA, it is possible to easily find where the tip of the needle attains when the needle is inserted as it is.

Incidentally, in the aforementioned embodiments and other embodiments, the structure is such that the paracentetic adapter 101 for inserting the paracentetic needle 100 is attached on the ultrasonic probe 1 and the direction (angle) for guiding the paracentisis needle 100 is fixed. However, the present invention is not limited thereto. For example, a structure can be adopted in which a rotation mechanism or the like is added in which the angle of the paracentetic adapter 101 can be arbitrarily changed automatically or by the hand with respect to the ultrasonic probe 1 thereby making it possible to change the angle of the paracentetic needle 100 when required. In this case, information on the angle of the paracentetic needle is preferably input to the side of the system main body 2 from the side of the paracentetic adapter 101.

What is claimed is:

1. An ultrasonic diagnosis apparatus comprising:
    a plurality of ultrasonic transducers arranged two-dimensionally, the ultrasonic transducers transmitting ultrasonic beams to a object being examined and receiving ultrasonic echo signals reflected by the object;
    means for obtaining the ultrasonic echo signals from the ultrasonic transducers by three-dimensionally scanning a target of the object with each of said ultrasonic beams;
    means for generating in real time three-dimensional data with respect to at least one of structure information and blood flow information in said object on a basis of the ultrasonic echo signals;
    means for generating in real time image information including at least one of a two-dimensional tomographic image and a three-dimensional projection image on a basis of the three-dimensional data; and
    means for displaying navigation information for navigating a puncture needle toward the target of the object on a basis of the image information,
    wherein said displaying means comprises:
        tracing means for detecting a position at each movement of the puncture needle inserted into the aforementioned object thereby tracing a track of the movement of the puncture needle, and
        means for changing in real time an image display condition so that a travel state of the puncture needle toward the target within said object can be recognized in said image, and
    wherein said tracing means comprises:
        a signal generator provided at a tip part of the puncture needle,
        means for receiving individually a transmission signal with at least three ultrasonic transducers out of said plurality of ultrasonic transducers, and
        means for inferring a position of the tip part of the puncture needle where said signal generator is provided on a basis of a difference in respective arrival times of respective received signals.

2. The ultrasonic diagnosis apparatus according to claim 1, wherein said image display condition includes a condition for displaying together a two-dimensional tomographic image of an arbitrary cross section inside of said object and a three-dimensional projection image projected along a direction which is along a line connecting an insertion point and the tip of the puncture needle.

3. The ultrasonic diagnosis apparatus according to claim 2, wherein said image display condition includes a condition for displaying in said three-dimensional projection image a tomographic image of a cross section vertical with respect to the travel direction of said paracentetic needle.

4. The ultrasonic diagnosis apparatus according to claim 3, further comprising a first marker display means for displaying a marker on at least one of said two-dimensional tomographic image and the three-dimensional projection image.

5. The ultrasonic diagnosis apparatus according to claim 4, wherein first marker display means comprises means for displaying a marker showing the position of the cross section of the tomographic image in said three-dimensional projection image in said two-dimensional tomographic image.

6. The ultrasonic diagnosis apparatus according to claim 4, wherein said first marker display means comprises means for displaying a marker showing the position of the cross section of said two-dimensional tomographic image in said three-dimensional projection image.

7. An ultrasonic diagnosis apparatus comprising:
    a plurality of ultrasonic transducers arranged two-dimensionally, the ultrasonic transducers transmitting ultrasonic beams to a object being examined and receiving ultrasonic echo signals reflected by the object;
    means for obtaining the ultrasonic echo signals from the ultrasonic transducers by three-dimensionally scanning a target of the object with each of said ultrasonic beams;
    means for generating in real time three-dimensional data with respect to at least one of structure information and blood flow information in said object on a basis of the ultrasonic echo signals;

means for generating in real time image information including at least one of a two-dimensional tomographic image and a three-dimensional projection image on a basis of the three-dimensional data; and means for displaying navigation information for navigating a puncture needle toward the target of the object on a basis of the image information;

wherein said displaying means comprises:

tracing means for detecting a position at each movement of the puncture needle inserted into the aforementioned object thereby tracing a track of the movement of the puncture needle, and means for changing in real time an image display condition so that a travel state of the puncture needle toward the target within said object can be recognized in said image, wherein said tracing means comprises:

a plurality of signal generators provided at a plurality of different locations on the puncture needle and configured to generate at least one of a signal with different signal waveforms which can be mutually recognized and a signal at mutually different transmission timings, means for receiving individually transmission signals from each of the signal generators with at least three ultrasonic transducers of the plurality of the ultrasonic transducers, and means for inferring positions of the plurality of different locations of the signal generators on the puncture needle on a basis of the respective signal arrival times of respective signals received by the receiving means.

8. An ultrasonic diagnosis apparatus comprising:

a plurality of ultrasonic transducers arranged two-dimensionally, the ultrasonic transducers transmitting ultrasonic beams to a object being examined and receiving ultrasonic echo signals reflected by the object;

means for obtaining the ultrasonic echo signals from the ultrasonic transducers by three-dimensionally scanning a target of the object with each of said ultrasonic beams;

means for generating in real time three-dimensional data with respect to at least one of structure information and blood flow information in said object on a basis of the ultrasonic echo signals;

means for generating in real time image information including at least one of a two-dimensional tomographic image and a three-dimensional projection image on a basis of the three-dimensional data; and means for displaying navigation information for navigating a puncture needle toward the target of the object on a basis of the image information, wherein said displaying means comprises:

tracing means for detecting a position at each movement of the puncture needle inserted into the aforementioned object thereby tracing a track of the movement of the puncture needle, and means for changing in real time an image display condition so that a travel state of the puncture needle toward the target within said object can be recognized in said image, wherein said image display condition includes a condition for displaying a two-dimensional tomographic image, and wherein said two-dimensional tomographic image is a two-dimensional tomographic image of a cross section whose position is based on a tip position of the puncture needle and a moving direction is determined on a basis of tip positions of the puncture needle.

9. The ultrasonic diagnosis apparatus according to claim 8, wherein said cross section is a cross section which passes through the position of the tip of said puncture needle and a straight line along a travel direction of the puncture needle.

10. The ultrasonic diagnosis apparatus according to claim 8, wherein said cross section is a cross section which passes through a straight line connecting an epidermal insertion point of said puncture needle into an inside of said object and the position of the tip of said puncture needle.

11. The ultrasonic diagnosis apparatus according to claim 8, wherein said cross section is a cross section which includes an insertion point of said puncture needle into said object, the position of the tip of the puncture needle, and a reference point which is regulated in advance.

12. The ultrasonic diagnosis apparatus according to claim 11, wherein said reference point is a center of gravity of the arrangement surface of said ultrasonic transducers.

13. The ultrasonic diagnosis apparatus according to claim 8, wherein said cross section is a cross section which passes through a straight line recursion line obtained from the position of the tip of said puncture needle and a normal line with respect to an arrangement surface of said ultrasonic transducers.

14. The ultrasonic diagnosis apparatus according to claim 8, wherein said cross section is a cross section which includes a straight line recursion line obtained from the track of the position of the tip of said puncture needle and a reference point which is regulated in advance.

15. The ultrasonic diagnosis apparatus according to claim 14, wherein said reference point is the center of gravity of the arrangement surface of said ultrasonic transducer.

16. An ultrasonic diagnosis apparatus comprising:

a plurality of ultrasonic transducers arranged two-dimensionally, the ultrasonic transducers transmitting ultrasonic beams to a object being examined and receiving ultrasonic echo signals reflected by the object;

means for obtaining the ultrasonic echo signals from the ultrasonic transducers by three-dimensionally scanning a target of the object with each of said ultrasonic beams;

means for generating in real time three-dimensional data with respect to at least one of structure information and blood flow information in said object on a basis of the ultrasonic echo signals;

means for generating in real time image information including at least one of a two-dimensional tomographic image and a three-dimensional projection image on a basis of the three-dimensional data; and means for displaying navigation information for navigating a puncture needle toward the target of the object on a basis of the image information, wherein said displaying means comprises:

tracing means for detecting a position at each movement of the puncture needle inserted into the aforementioned object thereby tracing a track of the movement of the puncture needle, and means for changing in real time an image display condition so that a travel state of the puncture needle toward the target within said object can be recognized in said image, wherein said image display condition includes a condition for displaying a two-dimensional tomographic image, wherein said two-dimensional tomographic image is a two-dimensional tomographic image of a cross section whose position is based on a tip position of the puncture needle and a moving direction determined on a basis of tip positions of the puncture needle;

said apparatus further comprising:
display means which visibly displays on said two-dimensional image the position of the puncture needle as separated from said cross section.

17. The ultrasonic diagnosis according to claim 16, wherein said display means comprises:
means for displaying on said two-dimensional tomographic image said puncture needle by changing at least one of a color and a luminance so that both sides sandwiching said cross section are individually recognized on said two-dimensional image.

18. The ultrasonic diagnosis apparatus according to claim 17, wherein said display means comprises:
means for displaying on said two-dimensional tomographic image said puncture needle by changing at least one of a color and a luminance so that a distance separated from said cross section is recognized on said two-dimensional image.

19. An ultrasonic diagnosis apparatus comprising:
a plurality of ultrasonic transducers arranged two-dimensionally, the ultrasonic transducers transmitting ultrasonic beams to a object being examined and receiving ultrasonic echo signals reflected by the object;
means for obtaining the ultrasonic echo signals from the ultrasonic transducers by three-dimensionally scanning a target of the object with each of said ultrasonic beams;
means for generating in real time three-dimensional data with respect to at least one of structure information and blood flow information in said object on a basis of the ultrasonic echo signals;
means for generating in real time image information including at least one of a two-dimensional tomographic image and a three-dimensional projection image on a basis of the three-dimensional data; and
means for displaying navigation information for navigating a puncture needle toward the target of the object on a basis of the image information,
wherein said displaying means comprises:
tracing means for detecting a position at each movement of the puncture needle inserted into the aforementioned object thereby tracing a track of the movement of the puncture needle, and
means for changing in real time an image display condition so that a travel state of the puncture needle toward the target within said object can be recognized in said image,
wherein said image display condition includes a condition for displaying a two-dimensional tomographic image,
wherein said two-dimensional tomographic image is a two-dimensional tomographic image of a cress section whose position is based on a tip position of the puncture needle and a moving direction is determined on a basis of tip positions of the puncture needle, and
wherein said image display condition includes a condition for displaying a three-dimensional projection image projected along a direction which is along a line connecting an insertion point and the tip of the puncture needle.

20. The ultrasonic diagnosis apparatus according to claim 19, wherein said image display condition includes a condition for displaying in said three-dimensional projection image a tomographic image of a cross section vertical with respect to a travel direction of said puncture needle.

21. The ultrasonic diagnosis apparatus according to claim 20, wherein said tomographic image is a tomographic image of a cross section at a plurality of mutually different locations which are constituted so that a cross-sectional tomographic image can be arbitrarily selected along the travel direction of said puncture needle.

22. The ultrasonic diagnosis apparatus according to claim 20, wherein said tomographic image is a tomographic image of a cross section which passes through said target.

23. The ultrasonic diagnosis apparatus according to claim 20, wherein said tomographic image is a tomographic image of a cross section which is constituted so as to follow a movement of the tip position of said puncture needle.

24. The ultrasonic diagnosis apparatus according to claim 19, wherein said three-dimensional projection image displays at least one of a running of blood vessels inside of said object, the target, and said puncture needle.

25. The ultrasonic diagnosis apparatus according to claim 19, further comprising:
a second marker display means for displaying on said three-dimensional projection image a marker showing a correspondence of a mutual position relation between a direction of two axes which forms two-dimensional planes of said three-dimensional projection image and a state in which the object is observed from the epidermis thereof.

26. The ultrasonic diagnosis apparatus according to claim 25, wherein said second marker display means comprises:
means for displaying on said three-dimensional projection image a marker connecting an epidermal insertion point of said puncture needle with a reference point which is set in advance on said plurality of ultrasonic beams transducers.

27. The ultrasonic diagnosis apparatus according to claim 25, wherein said second marker display means comprises:
an instrument for direction instruction which is rotatably attached in the vicinity of the insertion point of said puncture needle and which allows recognition of the attachment direction thereof; and
means for displaying a marker set in accordance with the instrument by corresponding a mutual position relation between an attachment direction of the instrument and said three-dimensional projection image.

28. The ultrasonic diagnosis apparatus according to claim 19:
wherein said three-dimensional projection image includes a three-dimensional projection image of blood vessels, a three-dimensional projection image of the puncture needle, and a B mode tomographic image of a lesion which is selected as the target.

29. The ultrasonic diagnosis apparatus according to claim 19, wherein said three-dimensional projection image includes a three-dimensional projection image of blood vessels, a three-dimensional projection image of the puncture needle, and a B mode three-dimensional image of a lesion which is selected as the target.

30. The ultrasonic diagnosis apparatus according to claim 19, wherein said three-dimensional projection image includes a three-dimensional projection image of blood vessels, a three-dimensional projection image of the puncture needle, a B mode three-dimensional image of a lesion which is selected as the target, and B mode puncture image of a tip part of the puncture needle.

* * * * *

UNITED STATES PATENT AND TRADEMARK OFFICE
CERTIFICATE OF CORRECTION

PATENT NO. : 6,336,899 B1
DATED : January 8, 2002
INVENTOR(S) : Nobuo Yamazaki

It is certified that error appears in the above-identified patent and that said Letters Patent is hereby corrected as shown below:

Column 17,
Line 38, change, "a" to -- an --;
Line 49 through line 50, change, "real time image information including at least one of" to --real time on a basis of the three dimensional data --;
Line 51 through 52, delete, "and a three-dimensional projection image on a basis of the three-dimensional data";
Line 54 through line 55, delete, "toward the target of the object on a basis of the image information";
Line 57, delete, "tracing",
Line 58 through line 60, change, "into the aforementioned object thereby tracing a track of the movement of the puncture needle, and" to --into the object, and;--;

Column 17, line 61 through Column 18, line 5,
Delete, "an image display condition so that a travel state of the puncture needle toward the target within said object can be recognized in said image, wherein said image display condition includes a condition for displaying a two-dimensional tomographic image, and wherein said two-dimensional tomographic image is a two-dimensional tomographic image of a cross section whose position is based on a tip position of the puncture needle and a moving direction is determined on a basis of tip".

Column 18,
Line 5, change, "positions" to -- a position of the two-dimensional tomographic image based on the position --;
Line 39, change "a" to -- an --;
Lines 49 through 50, change "real time image information including at least one of" to --real time on a basis of the three-dimensional data";
Line 52 through line 53, delete "and a three-dimensional projection image on a basis of the three-dimensional data";
Line 55 through line 56, delete "toward the target of the object on a basis of the image information"
Line 57, change "displaying" to -- display --;
Line 58, delete "tracing"
Line 59 through line 61, change "into the aforementioned object thereby tracing a track of the movement of the puncture needle, and" to -- into the object; and --;
Line 62 through 67, delete "an image display condition so that a travel state of the puncture needle toward the target within said object can be recognized in said image, wherein said image display condition includes a condition for displaying a two-dimensional tomographic image,";

UNITED STATES PATENT AND TRADEMARK OFFICE
CERTIFICATE OF CORRECTION

PATENT NO.   : 6,336,899 B1
DATED        : January 8, 2002
INVENTOR(S)  : Nobuo Yamazaki It is certified that error appears in the above-identified patent and that said Letters Patent is hereby corrected as shown below:

Column 19,
Line 1 through line 5, change "wherein said two-dimensional tomographic image is a two-dimensional tomographic image of a cross section whose position is based on a tip position of the puncture needle and a moving direction determined on a basis of tip positions of the puncture needle;" to -- a position of the two-dimensional tomographic image based on the positions of the puncture needle; --;
Line 7, change "displaying" to -- display --;
Line 9, change "said cross section." to -- a cross section whose position is based on a tip position of the puncture needle. --;
Line 27, change "a" to "--an- ";
Line 38 through line 40, delete "image information including at least one of a two-dimensional tomographic image and";
Line 43 through line 44, delete "toward the target of the object on a basis of the image information";
Line 45, change "displaying" to -- display --;
Line 46, delete "tracing";
Line 47 through line 48, delete "aforementioned";
Line 48 through line 49, delete "thereby tracing a track of the movement of the puncture needle,";
Lines 50 through line 62, delete "means for changing in real time an image display condition so that a travel state of the puncture needle toward the target within said object can be recognized in said image, wherein said image display condition includes a condition for displaying a two-dimensional tomographic image, wherein said two-dimensional tomographic image is a two-dimensional tomographic image of a cress section whose position is based on a tip position of the puncture needle and a moving direction is determined on a basis of tip positions of the puncture needle, and"
Line 63 through line 64, delete "for displaying" and insert -- means for displaying in real time --;
Line 65, delete "a direction which is along a line connecting an insertion point and the tip of the puncture needle" and insert -- a moving direction determined on a basis of the position of the puncture needle, --; and

UNITED STATES PATENT AND TRADEMARK OFFICE
CERTIFICATE OF CORRECTION

PATENT NO. : 6,336,899 B1
DATED : January 8, 2002
INVENTOR(S) : Nobuo Yamazaki

It is certified that error appears in the above-identified patent and that said Letters Patent is hereby corrected as shown below:

Column 20,
Lines 2 through 3, delete "image display condition includes a condition means" and insert -- means --;
Lines 8 through 11, delete "at a plurality of mutually different locations which are constituted so that a cross-section tomographic image can be arbitrarily selected along the travel direction"

Signed and Sealed this

Twentieth Day of July, 2004

JON W. DUDAS
*Acting Director of the United States Patent and Trademark Office*